(12) United States Patent
Raghavan et al.

(10) Patent No.: US 8,545,405 B2
(45) Date of Patent: ***Oct. 1, 2013

(54) DEVICE, METHODS, AND CONTROL FOR SONIC GUIDANCE OF MOLECULES AND OTHER MATERIAL UTILIZING TIME-REVERSAL ACOUSTICS

(75) Inventors: Raghu Raghavan, Baltimore, MD (US); Armen P. Sarvazyan, Lambertville, NJ (US)

(73) Assignee: Therataxis, LLC, Baltimore, MD (US)

( * ) Notice: Subject to any disclaimer, the term of this patent is extended or adjusted under 35 U.S.C. 154(b) by 1305 days.

This patent is subject to a terminal disclaimer.

(21) Appl. No.: 12/319,311

(22) Filed: Jan. 6, 2009

(65) Prior Publication Data

US 2009/0270790 A1 Oct. 29, 2009

Related U.S. Application Data

(60) Provisional application No. 61/125,210, filed on Apr. 23, 2008.

(51) Int. Cl.
*A61B 8/00* (2006.01)

(52) U.S. Cl.
USPC .......................... 600/437; 600/439; 600/447

(58) Field of Classification Search
USPC ........................... 600/439, 437, 447
See application file for complete search history.

(56) References Cited

U.S. PATENT DOCUMENTS

| | | | |
|---|---|---|---|
| 4,503,708 A | 3/1985 | Kino et al. | |
| 5,092,336 A | 3/1992 | Fink | |
| 5,428,999 A | 7/1995 | Fink | |
| 5,752,515 A | 5/1998 | Jolesz et al. | |
| 6,733,450 B1 * | 5/2004 | Alexandrov et al. | 600/439 |
| 7,101,337 B2 | 9/2006 | Aubry et al. | |
| 7,134,438 B2 | 11/2006 | Makower et al. | |
| 7,412,276 B2 | 8/2008 | Halperin et al. | |
| 7,713,200 B1 * | 5/2010 | Sarvazyan et al. | 600/437 |
| 2004/0054357 A1 | 3/2004 | O'Donnell | |
| 2004/0059265 A1 * | 3/2004 | Candy et al. | 601/2 |
| 2004/0162507 A1 * | 8/2004 | Govari | 601/2 |
| 2004/0267234 A1 | 12/2004 | Heart et al. | |
| 2005/0277824 A1 | 12/2005 | Aubry et al. | |
| 2006/0241529 A1 | 10/2006 | Hynynen et al. | |
| 2007/0038060 A1 * | 2/2007 | Cerwin et al. | 600/407 |
| 2011/0144493 A1 * | 6/2011 | Sarvazyan | 600/439 |

OTHER PUBLICATIONS

PCT Written Opinion of the ISA and International Search Report for related PCT patent application PCT/US2010/000035.

* cited by examiner

*Primary Examiner* — Long V. Le
*Assistant Examiner* — Helene Bor
(74) *Attorney, Agent, or Firm* — Mark A. Litman & Associates, P.A.

(57) ABSTRACT

Acoustic waves exhibit force that pushes objects along the direction of sound propagation. Precise motions require well-focused beams. The technique of time-reversal acoustics (TRA) overcomes beam distortions introduced by propagation along irregular paths to focus sound without knowledge of the medium properties. TRA requires a small receiver to be placed at a point of desired focus. The invention disclosed refines TRA by introducing data matching schemes to extend the points of focus beyond the location points of the receivers. With as few as two receivers, a large region can be manipulated with well-focused acoustic beams and with no receiver at a desired point of focus. Applications are described in drug delivery in medicine; environmental fluid contaminant control; and in oil exploration, for retrieving oil stuck in underground pockets.

29 Claims, 13 Drawing Sheets

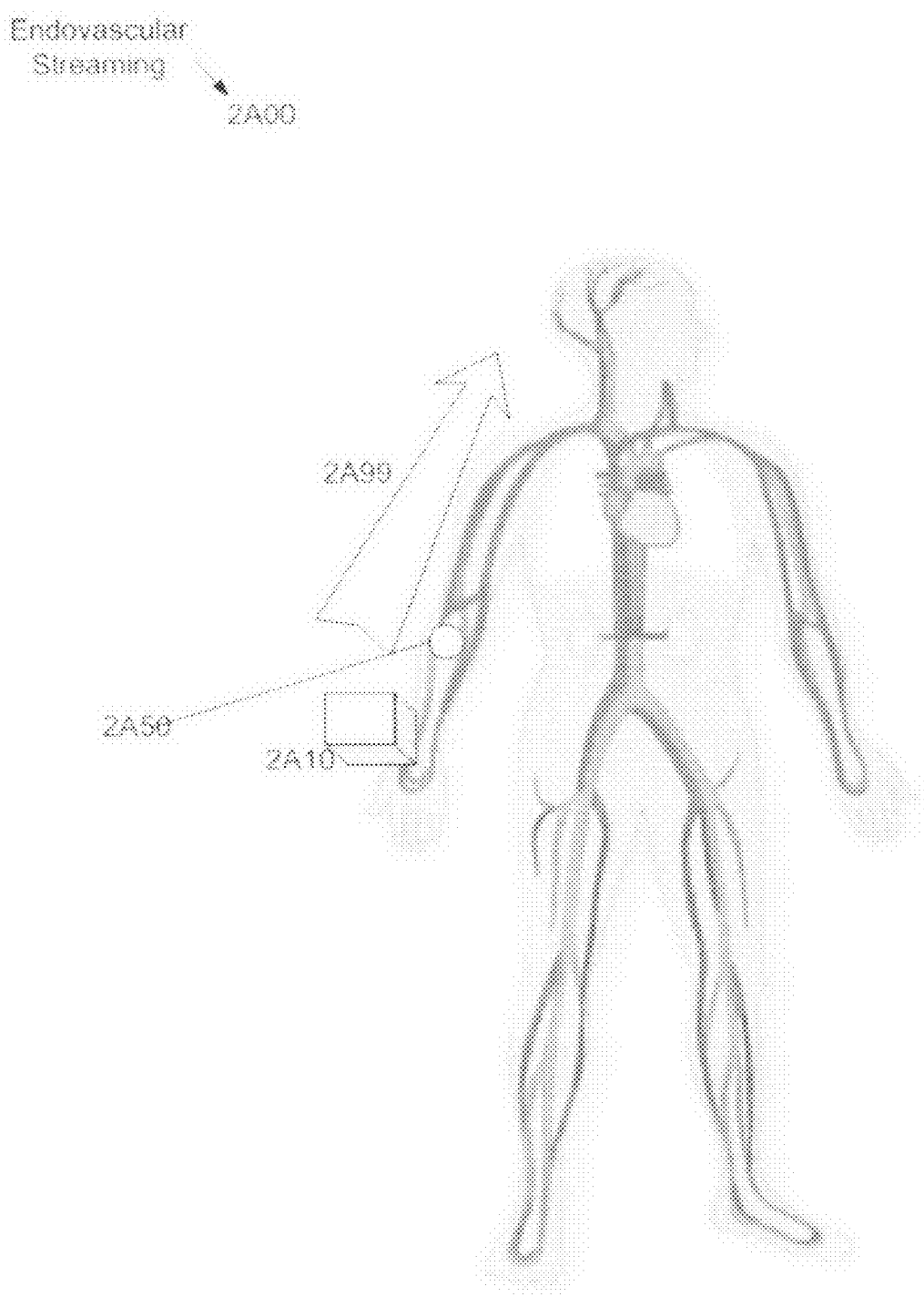

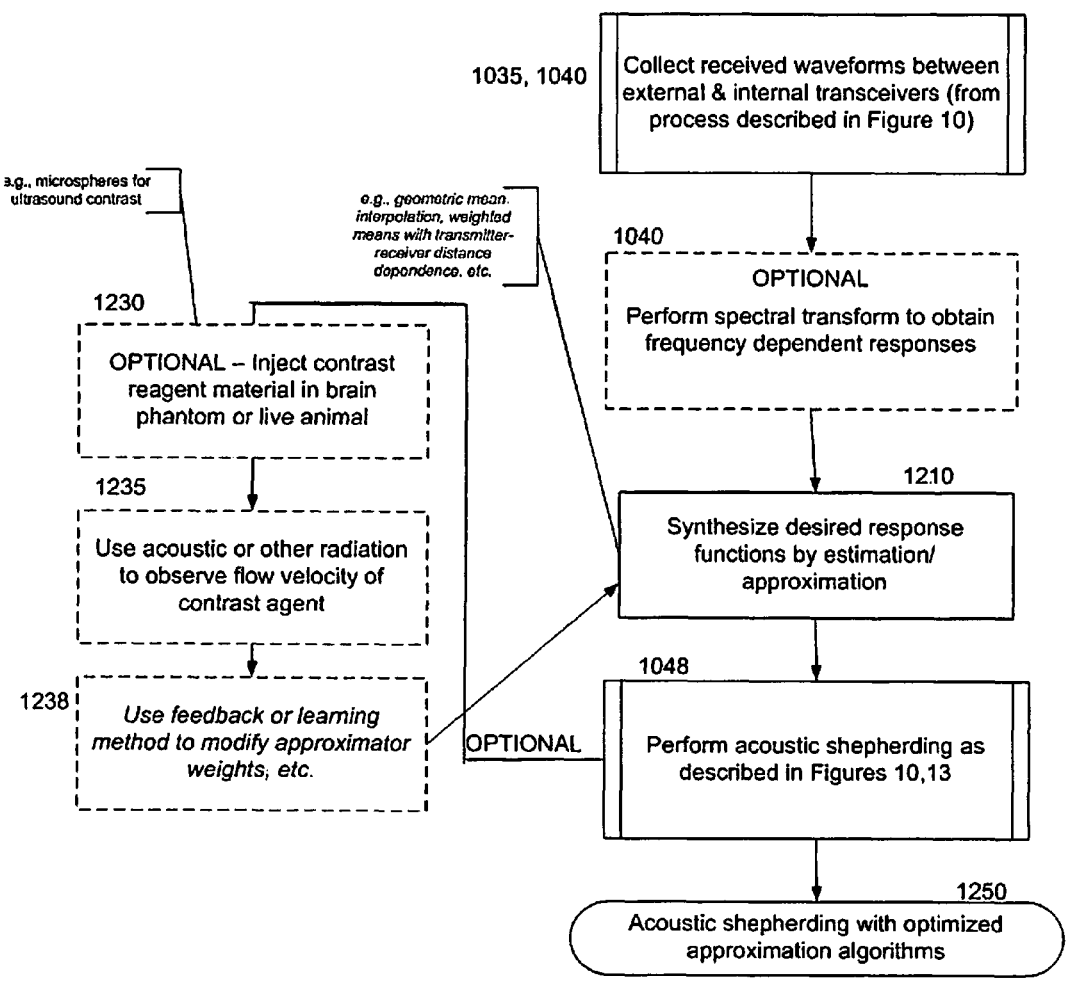

DEVICE, METHODS, AND CONTROL FOR SONIC GUIDANCE OF MOLECULES AND OTHER MATERIAL UTILIZING TIME-REVERSAL ACOUSTICS

RELATED APPLICATIONS DATA

This Application claims priority from U.S. Provisional Application Ser. No. 61/125,210 dated Apr. 23, 2008, filed 28 Apr. 2008.

BACKGROUND OF THE INVENTION

1. Field of the Invention

The invention relates to the field of guiding materials in porous and other media, particularly the delivery and guidance of image-enhancing or active ingredients into tissue, especially tissue of patients. Its primary application is to guide therapeutic substances which are introduced into the body by the use of ultrasound applied from an array of one or more transducers to induce acoustic radiation force and streaming of the interstitial fluid in brain parenchyma.

We shall refer to the suite of applications and the several embodiments of this invention in the field of guidance and control of the flow of materials in porous media under the generic term Acoustic Shepherding.

2. Background of the Art

Chemotherapeutic agents are injected into the body with the intent of treating disease. For example, biologically active materials may be injected into the body with the goal of killing or deactivating cells within a tumor mass. Such materials can also be injected or infused in solution into the brain to treat cancer. A problem arises since the infusate may not flow efficiently along an internal body path that leads directly to the targeted mass. Moreover, the target itself may finally be reached after an unacceptably prolonged period because of natural delays in passive diffusion or uncontrolled flow of body fluids. These delays are particularly important in the long term, since endogenous bulk flow is likely to be a significant method of transmission of molecules and even cells in the presence of injury such as edema from tumors, trauma, or hemorrhagic stroke. Such edema cause significant opening of the extracellular spaces along the tracts of white matter such as the corpus callosum, optical fiber tracts, and so on and these provide flow paths for the introduced therapeutic particles. Another disadvantage of direct infusate is that, short of potentially dangerous chemical intervention (due to undesired side effects), the characteristic distance over which the pressure and the velocity are not negligible is dependent on the distribution of blood vessels and the permeability to hydrophilic plasma proteins which are outside the control of the infusion system parameters, thus leaving only the flow rate or the pressure of the infusion alone to drive the fluid. Of course, these too have a very limited range over which they may be varied since too low a flow rate means that the distribution of the therapeutic molecule will be diffusion and loss dominated resulting in poor spread; while, on the other hand, too high a flow rate might mean disruption to brain processes and architecture, and loss of infusate through white matter or CSF pathways.

Ultrasound methods have been used both for imaging and therapy. Most pertinent to this invention have been reports on the enhancement of drug penetration into the brain when catheterization procedures introducing drug into the blood vessels have also included ultrasound irradiation at diagnostic or higher levels: increased penetration of the drug into the brain has been noted. Such studies have been focused on opening the blood brain barrier.

On the other hand, the phenomenon known as acoustic streaming has been known for more than a century, following the pioneering treatment of Lord Rayleigh. Acoustic streaming is due to dissipation of acoustic wave energy in a medium, and the induced fluid velocity depends on the mechanism by which the energy is dissipated. In a medium such as the brain, with compressible compartments, extracellular fluid with narrow channels, and so on, it is expected that a variety of mechanisms will contribute to the overall streaming. As a simple illustrative example, consider a streaming velocity V in the direction of propagation of an acoustic signal. In magnitude, it has the form $V=A\alpha I/\mu c$ where A is a number that depends on details of the boundary conditions and geometries of the problem, $\alpha$ is the attenuation coefficient of the acoustic intensity at the frequency in question, I is the intensity of the sound wave at the point in question, $\mu$ is the viscosity of the fluid, and c is the velocity of sound. The attenuation coefficient $\alpha$ is frequency dependent, being often linearly or quadratically increasing in frequency depending on the pertinent attenuation mechanism. If a number of mechanisms contribute to the overall dissipation of energy, each of these mechanisms will contribute to a streaming velocity. Thus the actual magnitudes and directions of streaming velocity in the brain will call for an appropriate protocol, such as hand-in-hand development of experimental test and theoretical setup of the equations of fluid flow in a porous medium subject to acoustic irradiation that can be solved only via computer analysis of the acoustic equations.

To summarize, while direct injection into brain parenchyma is being used, thus bypassing the blood-brain barrier to penetration of drugs intended for action in the Central Nervous System (CNS), the resulting drug distribution is difficult to control. Ultrasound has been tested for affecting the permeability of the blood brain barrier, and acoustic streaming has been known in the theory of porous media studied by civil engineers and the like. Time reversal and related techniques based on the reciprocity of Green's function for equations describing wave propagation have been proposed and developed, especially by Mathias Fink et al. for medical applications related to destroying select targets within tissue and especially brain tissue. The following two subsections give further references to the background art.

The explanation, apparatus enablement, and background on ultrasound (acoustic) enhancement of mass flow, of reversible opening of the blood brain barrier, of time reversal techniques, ultrasound emission and the like are described for example in "Acoustic Enhancement of Diffusion in a Porous Material," Haydock, David and Yeomans, J. M., *Ultrasonics*, 41, (2003) 531-538; "The Mechanism of Generation of Acoustic Streaming," Mitome, Hideto, Electronics and Communications in Japan, Part 3, Vol. 81, No. 10, 1998; "Non-Invasive, Transcranial and Localized Opening of the Blood-Brain Barrier using Focused Ultrasound in Mice," *Ultrasound in Med & Biol.*, Choi, James J. et al., Vol. 33, No. 1, pp. 95-104, 2007; "Time-Reversal Acoustics in Biomedical Engineering," Fink, Matthias, et al., *Annu. Rev. Biomed Eng.*, 2003, Vol. 5, pp. 465-497; "Spatio-Temporal Coding in Complex media for Optimum Beamforming: The Iterative Time-Reversal Approach," Montaldo, Gabriel, et al., *IEEE Transactions on Ultrasonics, Ferroelectrics, and Frequency Control*, Vol. 52, No. 2, February 2005; "Experimental Demonstration of Non-Invasive Transskull Adaptive Focusing Based on Prior Computed Tomography Scans," Aubrey, J. F. et al., *J. Acoust. Soc. Am.*, 113, (1), January 2003; "Adaptive Focusing for Transcranial Ultrasound Imaging Using Dual Arrays," Vigno, F. et al., *J. Acoust. Soc. Am.*, 120, (5), November 2006; "High Power Transcranial Beam Steering for Ultrasonic Brain Therapy," Pernot, M. et al., *Phys Med. Biol.*, 48 (2003) 2577-2589; "Prediction of the Skull Overheating During High Intensity Focused Ultrasound Transcranial Brain Therapy," Pernot, M. et al., 2004 IEEE Ultrasonics Symposium, pages 1005-1011; "Time Reversal of Ultrasonic Fields—Part I: Basic Principles," Fink, Mathias, *IEEE Transactions on Ultrasonics, Ferroelectrics, and Frequency Control*, Vol. 39, No. 5, September 1992; "Time-Reversal of Ultrasonic Fields—Part III: Theory of the Closed Time-Reversal Circuit," Cassereau, Didier and Fink, Mathias, *IEEE Transactions on Ultrasonics, Ferroelectrics, and Frequency Control*, Vol. 39, No. 5, September 1992; "Time Reversal of Ultrasonic Fields—Part III: Theory of the Closed Time-Reversal Circuit," Cassereau, Didier and Fink, Mathias, *IEEE Transactions on Ultrasonics, Ferroelectrics, and Frequency Control*, Vol. 39, No. 5, September 1992; "Optimal adaptive focusing through heterogeneous media with the minimally invasive inverse filter," Vignon, Francois and de Rosny, Julien and Aubry, Jean-Francois and Fink, Mathias, *Journal of the Acoustical Society of America*, Vol. 122, No. 5, November 2007, pages 2715-2724; "Spatial and temporal concentrating of energy in ultrasound systems by single transmitter using time-reversal principles," Sarvazyan, A. and Sutin, A., *Proceedings of World Congress on Ultrasonics*, Paris, pp. 863-866, Sep. 7-10, 2003: See also further material by Dr. Sarvazyan and his colleagues at the web site of Artann laboratories www.artannlabs.com; "Patterns of Thermal Deposition in the Skull During Transcranial Focused Ultrasound Surgery," Connor, C. W. and Hynynen, K., *IEEE Transactions on Ultrasonics, Ferroelectrics, and Frequency Control*, Vol. 51, No. 10, October 2004; and Published U.S. Patent Application 2004/0267234. "Brain Arterioles show more active vesicular transport of blood-borne tracer molecules than capillaries and venules after focused ultrasound-evoked opening of the blood-brain barrier", Sheikov, Nickolai and McDannold, Nathan and Jolesz, Ferenc and Zhang, Yong-Zhi and Tam, Karen, and Hynynen, Kullervo, *Ultrasound in Medicine and Biology*, vol. 32, pp 1399-1409 (2006). "Local and Reversible blood-brain barrier disruption by non-invasive focused ultrasound at frequencies suitable for trans-skull sonications", Hynynen, Kullervo and McDannold, Nathan and Sheikov, Nickolai and and Jolesz, Ferenc and Vikhodtseva, Natalia *NeuroImage*, vol. 24, pp 12-20 (2005). Hynynen, Kullervo and McDannold, Nathan and Vikhodtseva, Natalia and and Jolesz, Ferenc, Radiology, vol. 220, pp 640-646 (2001). "Spatio-temporal analysis of molecular delivery through the blood-brain barrier using focused ultrasound", Choi, J. J. and Pernot, M. and Brown, T. R. and Small, S. A. and Konofagou, E. E., *Physics in Medicine and Biology*, vol. 52, pp 5509-5530 (2007). "Piezo-electric materials for high frequency medical applications: a review", Shung, K. K. and Cannata, J. M. and Zhou, Q. F., *Journal of Electroceramics*, vol. 19, pp 139-145 (2007). "Unified Green's function retrieval by cross-correlation: connection with energy principles", Snieder, Roel and Wapenaar, Kees and Wegler, Ulrich, *Physical Review E* vol. 75 036103-1-14 (2007). An overview of the field titled "Time Reversal", by Anderson, Brian E., and Griffa, Michele, and Larmat, Carene, and Ulrich, Timothy J. and Johnson, Paul A. published in *Acoustics Today*, vo. 4, pp 1-16 (2008) is also available. These references are incorporated herein in their entireties to provide technical information in support of the present disclosure and claims. Another prominent worker in the field of time reversal acoustics is Armen Sanazyan and his team at Artann laboratories.

U.S. Pat. No. 5,752,515 (Ferenc A. Jolesz and Kullervo Hynynen) discloses a method and apparatus for directly applying ultrasound for the purposes of opening up the blood-brain barrier (sonoporation) and confirming the opening by the injection of a contrast agent observable with radiological imaging that is visible when the blood brain barrier is compromised. This, and other patents with Kullervo Hynynen as inventor, allow for the transducer to be placed adjacent to brain tissue, by the process of drilling a bore hole through the skull, to obviate the highly distorting effects of the skull.

U.S. Pat. No. 5,092,336 (Mathias Fink) discloses how to localize a reflective target within tissue by the application of ultrasound transmission from transceivers placed distally from the desired target, and subsequent application of time-reversal technology to process the signals reflected from the target, so that an ultrasound beam may be formed for the purposes of focusing the energy on the reflective target.

U.S. Pat. No. 5,428,999 (Mathias Fink) discloses further methods and processing schemes within the rubric of time reversal methods to localize reflective targets in tissue for the purposes of focusing ultrasound on these targets for therapeutic purposes.

U.S. Pat. No. 7,101,337 I (Jean-Francois Aubry, Mathias A. Fink, Mickael Tanter, and Jean-Louis Thomas) discloses a method for imaging, for example, brain tissue allowing for the dissipative heterogeneous acoustic properties of the skull, wherein the transceivers are outside the skull, acoustically coupled to it, and methods of signal processing are introduced to correct for the distortions produced by the skull so that the acoustic signals may propagate through the tissue and be received and decoded for imaging purposes.

U.S. Patent Application Publication 2004/0267234 "Implantable Ultrasound systems and methods for enhancing localized delivery of therapeutic systems" (Gill Heart and Axel Tolkowsky and Joe Brisken) discloses the application of intraparenchymal delivery of a therapeutic agent in solution, with an ultrasound transmitter inserted through a burr hole in the skull to the surface of the brain, coaxial with a catheter that is pumping the therapy-containing solution. The transmitted ultrasound then induces a further spread of the agent, beyond what would be obtainable from the pressure-driven infusion of the solution alone.

U.S. Patent Application Publication 2005/0277824 "Non-invasive method of obtaining a pre-determined acoustic wave field in an essentially uniform medium which is concealed by a bone barrier, imaging method and device for carrying out said methods" (Jean-Francois Aubry and Mathias Fink and Mickael Tanter) teaches a method for obtaining a desired sound field within the brain by means of echographic signal processing methods applied to signals transmitted and received by transceiver arrays positioned outside the skull.

U.S. Patent Application Publication 2006/0241529 "Adaptive Ultrasound Delivery System" (Kullervo Hynynen and Nathan McDannold) discloses a phased array of transceivers, the frequencies and positioning of which are adjusted till the desired opening of the blood brain barrier is achieved, as detected by contrast agent imaging.

All references cited are incorporated herein by reference in their entirety to support the technical nature of the disclosure.

SUMMARY OF THE INVENTION

The present technology relates to methods and apparatus used in conjunction with ultrasound imaging technology. The present inventions and disclosure relate to methods for controlling mass movement of delivered material within a patient. This control effect may be accomplished by methods, which for example may comprise:

at least one original signal of sound waves is transmitted from at least one array of transmitters outside of a field of interest in the patient;

the at least one original signal is received by at least one receiver within the field of interest as a received signal;

the at least one original signal is processed by time-reversal acoustic procedures to generate a mathematical and physical causal relationship between the original signal and the received signal;

the generated causal relationship is used to design a modified original signal that will produce a specific intended acoustic effect in the field of interest near the at least one receiver; and the modified original signal which is then transmitted from at least one of the at least one array of transmitters outside of the field of interest to modify mass movement of materials within the field of interest.

The present inventions and disclosure also relate to methods of controlling flow of material injected into tissue. This may be accomplished by the following non-limiting descriptions of methods comprising:

providing a set of at least one ultrasound transmitter array (s) located outside of the region of interest in the tissue;

providing at least one signal from the at least one ultrasound transmitter, which can be either internal or external to the field of interest and within and/or without a patient, if used in a medical procedure;

providing at least one receiver/transmitter located within the tissue; and implementing time-reversal acoustics by steps comprising a) recording the at least one signal from the at least one ultrasound transmitter as a pulse or pulse trains transmitted from the at least one transmitter in the array, b) modifying the received waveform in a pre-determined manner to affect an acoustic result within the tissue including estimation and approximation, data matching and fitting, Fourier or wavelet transforms, and other signal processing schemes c) time-reversing the modified signal to form a time-reversed waveform (first signal in, last out and last signal in, first out), d) further modifying the time-reversed waveform including scaling, normalization, and amplification in a pre-determined manner to affect an acoustic result within the tissue, and e) re-transmitting from the transmitter array as a modified waveform pulse.

The present technology disclosed herein also includes an ultrasound device or system for controlling the flow of material injected into a region of interest within tissue. This technology may comprise:

a) an array of at least one repositionable array of one or multiple ultrasound transmitters located outside of the region of interest of the tissue, b) output control for the transmitters causing pulse trains to be transmitted from the transmitter in the array, c) at least one receiver receiving the pulse train within the region of interest; and d) a processor capable of executing software contained in the processor of a computational scheme that computes mass flow based on known characteristics of at least some of skull and brain tissue, meninges and blood vessels, to simulate the received wave train at a designated point in tissue in the region of interest.

In addition, it is advantageous for speed of processing that the receivers be transceivers, i.e., have transmission capability in addition to receiving capability. Whenever feasible and safe in the applications, this will be assumed.

BRIEF DESCRIPTION OF THE FIGURES

FIG. 2A shows another endovascular embodiment of technology within the scope of the generic invention.

FIG. 9 shows a process by which data matching of response functions may be performed to allow Acoustic Shepherding at points intermediate between two or more receiver locations.

DETAILED DESCRIPTION OF THE INVENTION

Figure 1:
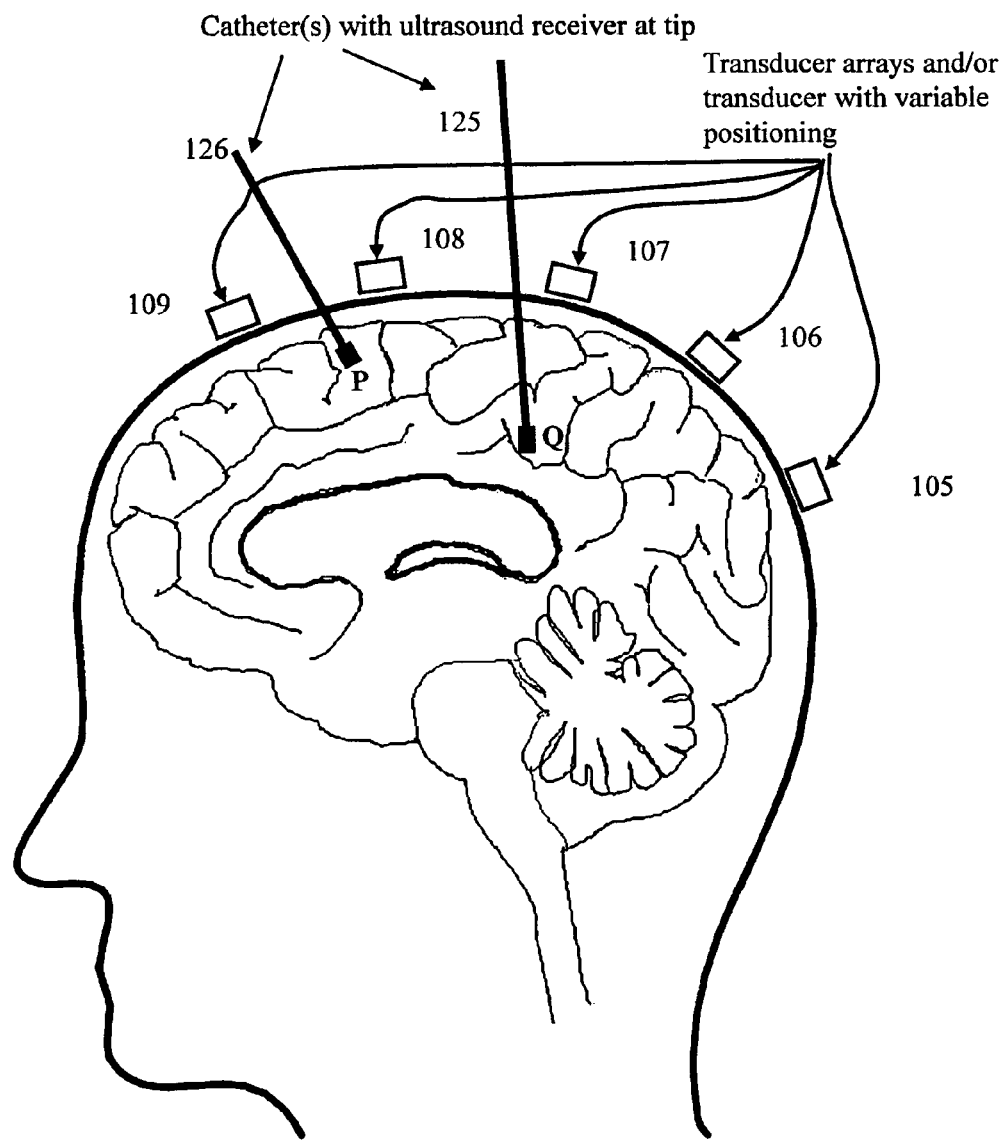
FIG. 1 shows a schematic representation of a procedure on a skull with some preferred embodiments of the invention.

The invention describes several embodiments and technologies that address sending a signal to a remote location somewhere off a grid of available sensors. Sending such a signal could be for purposes of communicating or irradiating of a certain region with sound for dislodging or moving an object by using acoustic/ultrasound vibrations, or for establishing a pressure gradient to encourage a packet of fluid (or materials suspended or dispersed or dissolved therein) to flow in a particular direction. Embodiments of the present invention for these and other applications are described herein.

One application is to guide therapeutic substances which are introduced into the body by the use of ultrasound applied from an array of one or more transducers to induce acoustic radiation force and streaming of the interstitial fluid in brain parenchyma. The beam is directed towards the target tissue to enhance fluid flow and transport the target material to the desired site more efficaciously and in a much shorter time than that occurring passively, or with pump-driven infusion alone, or due to endogenous bulk flow in the tissue. It will also concentrate flow more efficiently to the region of the desired treatment volume. Another important field of application of this invention is in distributing an infusate over the broad but thin area of cerebral cortex for possible treatment of neurological diseases such as Alzheimer's disease. The method can be additionally effective when the target tissue is imaged with acoustic, magnetic resonance (MR), or X-ray or computed tomographic (CT) imaging and related techniques. The method has further advantages when the flowing infusate can be imaged with acoustic, MR or CT techniques; such imaging can be enhanced by including small ultrasound, MR or CT contrast agents in the injected material.

Analogous problems also arise in fluid flow problems in the earth, either for retrieval of stuck oil, or for remediation of hazardous waste fluids from underground. The methods of the present invention are also applicable to these applications. For the cases of stuck oil and underground fluid contaminants, the methods currently available involve shaking large volumes of the ground simultaneously. This approach requires very large amounts of seismic energy input into the ground. The method introduced in this invention is very targeted and localized, and permits much smaller amounts of seismic energy to be input to achieve the same ends.

Another potential application of one of the embodiments of this invention is for data compression applications, both those related to the present applications such as drug perfusion or dislodging stuck underground oil or fluid contaminants and also to other applications to very large 2D and 3D seismic wave datasets used in the oil industry when searching for oil and gas underground. In the present technology, a method is described that includes a novel time-reversal procedure that has been developed by the inventors. The time reversal procedure as described makes use of the reciprocity of the acoustic Green's function to permit refocusing on a known (or possibly unknown) source location by recording a wave train received at a set of transducers, time-reversing these signals (first in last out, last in first out) and then rebroadcasting them back into the acoustic medium. If the signals received and recorded were from a single source, the reciprocity property of the wave equation effectively guarantees that some part of the time-reversed signal will indeed reconverge on the original source location.

In the present application of time-reversal acoustics, this invention also describes and uses soundwave interpolation. The use of modest amplitude acoustic focusing may be used to direct perfusion of drugs to desired locations within a body, and even lodged solids (even clots, thrombi or clot chips). A seismic application might be to dislodge oil, other fluids, or contaminants that are stuck underground and that should be encouraged to flow towards a particular well-bore for retrieval and subsequent disposal. Thus, at least one concern addressed in this invention is methodology to refocus sound or seismic energy back into a target medium at points other than the preferred at least two source points. In interpolation, therefore, a time reversed waveform is transmitted with interpolation of amplitudes so that the modified waveform pulse is received by the tissue at a desired point intermediate between at least two receiver/transmitter locations.

It is necessary that there are at least two sound sources be used for actual direction of material or that two points of emanation for sound sources be available for mapping of a region or one movable source so that two-directional signals are provided. In medicine, these might be placed within two or more catheters on opposite sides or in a surrounding perspective of a tumor, or a large region within which it is desired to provide a fairly uniform distribution of some drug or other fluid medication, or a single catheter with two projecting sound emitters may be used. In a seismic application, at least two well-spaced boreholes may be provided between which is a region where it is desired to create focused vibrations to dislodge a contaminant, or to encourage stuck oil or other fluids to flow. These two sound sources can each be used to send a signal from their current locations to an external array (outside the body in the medical application, or at the surface of the earth in the geophysical application). By using a short burst of sound, from each of these two transducers in turn, and subsequently recording the resulting signals at the external array, benchmark empirical response functions are established for the organ (or alternatively the host earth medium).

An underlying technology and technique preferably used in the practice of the claims are inventions generically described herein, and that may enable at least two features. Sound wave propagation and movement in liquid environments can be used to adjust duration and movement of mass within a liquid. That is, even though there may be significant and existing local forces (capillary action, Brownian motions, diffusion and other forces causing mass transfer within the liquid), proper application and focusing of sound waves in the liquid can alter movement of mass within the liquid by a controlled mechanism. The use of mathematical oversight concerning the spatial orientation of the wavefronts, and temporal arrangement as well as the physical properties of sound waves such as the magnitude or intensity using time-reversal acoustic techniques can provide significantly enhanced focus and quality/quantity to the transmission of sound waves, which will significantly enhance the performance of directed mass movement and/or persistence of movement within a liquid environment.

The term liquid environment is not specifically limited to large open areas of liquid, especially within a patient. The term includes not only liquid volume within vessels and ducts, but also intercellular and intracellular liquids. The forces applied to the masses in the liquid environments can be used to reduce or enhance existing mass transfer patterns in specific (targeted) locations so that mass within that liquid environment will persist longer, distribute more rapidly, or distribute more efficiently (i.e., with less loss of the directed effusate) in a desired direction and speed than ambient conditions allow. Similarly, in seismic application, the seismically induced pressure gradient causes in the pores of the earth medium (rock) to flow via Darog's law.

The inventions herein include methods, procedures, systems, apparatus and processes for influencing mass movement within liquid environments, especially movement of delivered materials within patients, especially catheter-delivered solids, liquids, suspensions, dispersions, emulsions or gels delivered to or from vessels in a patient.

There are at least three related technologies using the concepts of the present technology. Those three related technologies, each of which is one type of the single generic concept referred to as Acoustic Shepherding may be referred to herein as 1) Mass Movement Control, 2) Directed Mass Movement, and 3) Mass Movement Prevention. In a process of Mass Movement Control, the focused ultrasound is used to contain delivered material within a region of the field of interest of a patient by inducing localized pressure gradients and barriers. An aspect of the exercise of this first related technology is that first a planned focusing transmission of ultrasound or sonic waves has been generated by the underlying process described in the Brief Description of the Invention and explained in greater detail herein. Then, transmission of the focused ultrasound (by designed amplitude, frequency, pulse shape, pulse duration, intensity, directionality and other vectors defining the transmission), is used to restrain movement of delivered mass within the region of interest for the patient. This focused sound may be used essentially to retain a delivered mass (e.g., bolus, dose, dispersion, concentration or volume of material) approximately at a desired location. For example, if an active agent has been delivered into the putamen, adjacent to the white matter tracts of the internal capsule, enhanced liquid flow in the white matter region would dissipate that drug from that location within a period of time X under normal flow and fluid movement circumstances with a time X, which could be quite fast and not allow significant further filling of the putamen. The dissipation would theoretically (without significant flow in that region) be a radial mass migration of the material away from a center of the mass and away from the putamen. By providing focused sound waves emitted from transmitters focused antiparallel to a number of channels of movement away from the center of the mass, timed pulses can restrain mass movement by using acoustic pressure pulses to push back against the normal lines of mass migration.

Additionally, this technology of Mass Movement Control (focusing sound to produce directional flow) can be used to focus the propagation and absorption of transmitted ultrasound energy in a direction approximately parallel (e.g., ±30 degrees) towards a delivery end of a catheter, the ultrasound pushing delivered material distally, reducing backflow up the catheter. Backflow of this type occurs because the pressure from the flow pushes the tissue away from the catheter, allowing a tissue-free channel for fluid flow moving the material up the length of the catheter, and reducing the flow of fluid into the parenchyma itself. Therefore one broad aspect of the Mass Movement Control is to be able to direct ultrasound along the length of the catheter.

Another area of use for this technology after designing focused ultrasound transmissions from at least one transmitter array outside of the field of interest to at least one receiver within the field of interest is referred to as Directed Mass Movement. Directed Mass Movement is related to Mass Movement Control in that the focused ultrasound or sonic transmission is directed at delivered material, but instead of specifically attempting to restrain normal movement, a planned movement of the mass is intended, with the sonic forces causing portions of the delivered mass to move in a planned direction. For example, drug delivery within the brain is sometimes limited to accessible delivery locations because veins, arteries and capillaries are present at only specific locations and are not necessarily uniformly distributed. An operator must select an available vessel that is most convenient and most functionally located (e.g., one would not want to deliver material into a vessel a few cm from a target cite if the movement of liquid within the vessel is directed further away from the site). Having chosen an appropriate delivery vessel, the drug is delivered into and out of that vessel to the delivery site, and the Directed Mass Movement is performed by focusing pulses of the ultrasound according to a planned program that will actually cause movement of the delivered material in an intended direction based upon use of the focused acoustics and the plan.

An additional area of technology within the generic scope of the disclosed technology is referred to as Mass Movement prevention. This is obviously closely related to the first two specific technologies described above, but has a different flavor of application. In this application, material (drugs, indicators, dyes, markers, etc.) are delivered into a region where there are multiple available pathways for movement, as within the prostate. When materials are normally delivered into the prostate, there is a greater tendency for them to be removed by ducts going into the prostatic urethra, rather than being distributed within the prostate tissue itself. The original transmission time reversal acoustic analysis is performed on the region and an imaging plot of the region is taken so that location and direction of the ducts is evaluated. A planned ultrasound transmission application is designed to increase lateral (relative to the direction of movement of the fluid within the ducts) mass movement pressure so that material movement into the prostatic urethra can be reduced by application of forces away from the ducts, towards the point of delivery of the material.

One process useful for the treatment of the prostate is to practice the time-reversal and modified waveform technology described herein so that pressure is directed from inside the prostate outwardly to reduce amounts of fluids entering a prostatic urethra.

Another procedure is related to the underlying process described in the referenced "Non-Invasive, Transcranial and Localized Opening of the Blood-Brain Barrier using Focused Ultrasound in Mice," *Ultrasound in Med. & Biol.*, Choi, James J. et al., Vol. 33, No. 1, pp. 95-104, 2007, although the application of the present process is materially different in directing flow of material. The time-reversal acoustic (TRA) techniques described herein can be used in the process of Choi et al., but is greatly enhanced by the unique combination of the TRA analysis and reprogramming of the transmission of ultrasound to be used with the ultrasound procedure to open the Blood-Brain Barrier.

Descriptions of actual techniques and systems according to this novel technology include at least the following:

A method may be practiced to control flow of material provided to or in (e.g., delivered, carried, transferred, naturally generated, decomposition products and/or injected into) tissue. The manner of delivery is not critical as long as its location of delivery can be determined and/or controlled. The method may include steps comprising:

(i) providing at least one ultrasound transmitter, preferably as at least one array of ultrasound transmitters located outside of the region of interest in the tissue, preferably by the least invasive positioning of transmitter(s) (such as outside the body, such as in contact with or proximal to the skull or scalp in delivery of mass to the brain); the simplest phased array is at least three transmitters. The typical phased arrays have at least 8, at least 16, at least 32 and more typically 128 transmitters/receivers. One transducer can be used either/both as receiver or transmitter, but phasing preferably requires three or more transducers.

(ii) providing at least one phased signal from the at least one array of ultrasound transmitters, the signal being a sonic wave, sonic waveform or series of sonic waves/ waveforms that have known acoustic properties (e.g., frequency, amplitude, duration, energy, etc.);

(iii) providing at least one receiver/transmitter (acoustic transducer) located within the tissue, in receiving mode being capable of providing acoustic information that it receives to an operator of the system, including a memory device or processor, while in transmitting mode it can emit small amplitude pulses to be recorded by the external array(s) of transducers; and (iv) implementing time-reversal acoustics by steps comprising a) recording (or performing real time analysis without persistent recording, as with flash memory, field programmable gated array (FPGA), or ASIC chip) at least one signal from the at least one ultrasound transmitter as a pulse or pulse trains transmitted from the at least one transmitter in the array, b) modifying the virtual received waveform in a pre-determined manner, such as to define a preferred transmission protocol of phased array output that will have predicted or planned sonic activity in the vicinity of the receiver, c) time-reversing the modified waveform to form information of a virtual time-reversed waveform, d) modifying the virtual time-reversed waveform, which may include scaling, normalization, and amplification, in a pre-determined manner to affect an acoustic result within the tissue and e) re-transmitting from the transmitter array as a modified waveform pulse.

It would be a good idea from the point of view of timing to use the transducer inside the tissue also in a transmit mode for some of the initial setting up of the acoustic wave forms. This is explained in greater detail later herein.

In the practice of this type of method in medicine, the tissue is preferably brain parenchyma, and the external transmitter array is arranged on the outside of a skull of a live patient, and at least one receiver is at one or a set of pre-determined positions along an axis of one or more catheters introduced into the brain parenchyma. The term array is used, even where there may be a single transmitter to cover situations where a single transmitter is moved outside the region of interest, the various locations are noted, and separate transmissions from the same transmitter at different locations are used to develop phased sonic wave data used in the time-reversal acoustic treatment of the data to design sonic transmissions that will provide local mass movement control as desired and planned.

The method as described herein may include intraparenchymal introduction of therapeutic material performed within 10 cm, within 5 cm, within 5 cm, within 3 cm, within 2 cm and within 1 cm or less (e.g., within 5, 4, 3, 3 or 1 mm) of the at least one receiver in a region of tissue of interest in the overall process. The method as described herein preferably may be practiced with a single transducer array on the outside of the skull, or multiple (2, 3, 4, 5, 6) transmitter arrays outside of the skull or other region of interest in the patient. The preferred method is where the tissue is that of an internal organ (especially the brain) of a live patient and the receivers/transmitters are inserted into the tissue of interest. There may be more than one receiver/transmitter within the tissue, as for example, along an axis of a catheter, or at the tip of more than one catheter or cannula, and a transmission protocol for at least one transmitter array may introduce a time sequence of decreasing pressure amplitudes at various receiver locations, to induce a net influence on the direction or vectors of flow in a vicinity of at least one of the more than one receivers.

It should be appreciated at this point that time reversal is an important quality control in the performance of the sonication or sound wave procedures of the technology described herein. When a sound wave is transmitted into an object as amorphous or variable as a patient, the transmission and progression of the sound wave through a patient is highly affected by the specific properties of the path through the patient. In medical or mass delivery procedures, this variability must be considered in treatment of individual patients to optimize the medical results intended. The time-reversal acoustics use the known information of the transmission, the received information of that transmission at a specific location in the patient (in the vicinity of the receiver), and time reverses the received information to determine the actual sonic effect at the receiver from the actual transmission, and calculates and measures losses of the original signal and the properties of the received signals.

In particular, the causal response becomes known between the transmitting and receiving transducers. This information (also known as the Green's function between the two points) is the information required for establishing the desired protocols for intraparenchymal therapy delivery design. Based on this information, the location, direction and properties of subsequent transmissions can be planned or designed to provide specific acoustic results at the target location to be able to control mass movement within the liquid environment. Planning can also include movement of the location and/or distribution of transmitters, frequency of pulses, amplitude of pulses, duration of pulses, and the like at the target site. We note that time reversal allows us to focus without knowing the properties of the medium in detail. If we do know the properties of the medium, either by consulting existing databases, or by inference from other imaging methods such as magnetic resonance or computed tomographic imaging, then another approach to focusing would be by the technology known as "phased array technology." This ability of time reversal acoustics to provide a focus within the medium does not immediately extend to imaging the medium: there we do need to know medium properties. Although there has been discussion of extending time reversal methods to imaging, that is not within the field of this invention and we do not discuss it further.

In a non-limiting embodiment of this invention, the desired focus point is optimized by a learning method for estimating weights of local and acoustic parameters. Contrast agents visible under ultrasound may be con-infused with the desired intraparenchymal therapy, or infused just prior to the therapeutic procedure. The Acoustic Shepherding described in this invention may thus be monitored in real time. Several properties of waveforms including their phases in the array, their amplitudes, and other features are amenable to adjustment by learning algorithms including statistical estimation and neural network methods. A multiplicity of transmitters may be used to enhance amplitude of the pulse at a specific receiver location when a time-reversed waveform is provided to at least some of several transmitters, and the signal had been recorded at the specific receiver location.

Multiple receivers may be positioned along at least one catheter(s) and the catheter(s) may be introduced into blood vessels. The effect of the transmitted ultrasound reversed waveform is focused (e.g., optimized for the intended procedure), transmission of the focused transmitted waveform causing location specific alteration of blood brain barrier permeability so that drugs introduced into blood vessels is delivered into a central nervous system. The drug may be injected or otherwise delivered into a peripheral blood vessel and then it may enter into catheterized vessels by standard pharmacokinetic phenomena, and then controlled by the methods of the present technology. At least one algorithm in executed software preferably may be used to optimize the focused power for safe and appropriate blood brain barrier alteration. The software may further include consideration of pharmacokinetic phenomena to ensure adequate dosing and residence of the drug or therapeutic molecule in CNS tissue.

A modified waveform pulse may be received within or adjacent to a volume of the tissue at a desired point intermediate between at least two receiver locations so that a delivered portion of drugs is retained within the volume of the tissue for a length of time longer than predictable for diffusion and perfusion factors in the volume without transmission of the modified waveform. This procedure is referred to as mass transfer stabilization, as opposed to mass transfer focus.

The tissue targeted in these procedures is preferably brain parenchyma, and the transmitter array comprises multiple transmitters arranged outside of the skull. The application of the invention has been generically described in delivering a specified waveform to an intraparenchymal location where an ultrasound receiver is, or has been, placed. It is an aspect of this invention that the array of transmitters is placed outside the skull, and it is a key component of this device that we take advantage of the time reversal properties of the acoustic waves to deliver enough power to be efficacious within tissue without requiring significant power in the transmitter that could otherwise be damaging. It is equally an advantage of this invention that we do not need to use very low frequencies. The usual, and profound, disadvantages of ultrasound in brain imaging has been the "acoustic opacity" of the skull (due to the acoustic impedance mismatch and resulting high reflectivity) which often requires both high power and low frequencies for adequate transmission into the parenchyma and subsequent detection through the skull again. Here we are taking advantage of time reversal in "focusing" a time sequence of acoustic power to a "point" in both space and time. (This of course requires assumptions of time reversal acoustics to work well, which includes the dominance or importance of the phase relationships of the signals that combine after scattering and reflection over any differences of sound wave speeds and or inertial densities. Also, the impedance mismatch between skull and brain will still be an impediment to high transmissibility, but having multiple arrays of transmitters should help to overcome this problem.) Thus the requirement of sufficient power in the acoustic signal is reduced since we add up the integrated power in the time domain (i.e., the total transmitted energy over the duration of the pulse train) to provide higher power at the intended receiving point or location. For the same reason, we do not need to use low frequencies which, although they transmit better through the skull, are also unfortunately more dangerous, being known to cause cavitation in tissue. Thus the time reversal method allows us to use lower power from individual transmitter arrays, a less dangerous range of frequencies, and last but not least, place the transmitters outside the parenchyma. Devices which have multiple higher amplitude acoustic transmitters within parenchyma are believed liable to result in more adverse events than transmitter arrays that remain outside. The internal receivers/transmitters are for one-time use, while the external transmitter arrays can be more expensively constructed and are meant for multiple re-use.

In another unique practice within the scope of the generic technology described herein, the at least one receiver comprises encapsulated objects arranged at positions in blood vessels, the encapsulated objects being guided to the positions by magnetic stereotaxis; and then the ultrasound is focused by the time reversal for alteration of blood brain barrier permeability, causing drugs introduced into blood vessels to be delivered into central nervous system regions of the patient.

The methods herein may also be practiced where the tissue is brain parenchyma, the transmitter array is arranged on the outside of the skull, and the at least one receiver is an encapsulated object arranged at positions within brain tissue, the encapsulation having migration restraining physical elements of chemically active functionality to restrain migration of the receivers. Physical or chemical "tails" or migration impeding functionality may be added to the encapsulated object to reduce its migration, and the initial estimated focusing of ultrasound or other sonic transmissions used to gather original data may also control movement of the receivers. Long chemical tails such as polyoxyethylene polymers or copolymers (as with polyoxypropylene units), siloxane polymers, fluorinated polymers, polyamide polymer tails or other inert and biologically acceptable species may be used for the chemical and/or physical tails. Harmless soluble tails may be used with time dissolution of the tails and capsules after used, as with controlled dissolution polymers such as polyvinyl alcohol, polyoxyethylene polymers, polyvinylpyrrolidone, gelatin, polyamylose, and the like.

Additionally, enhancement of the movement of large particles such as viruses or cells may also be expected to be similarly controlled due to the acoustic radiation pressure on such particles themselves. This effect is expected to be negligible for small proteins, in which case the maximum benefit of the acoustic forces is on the fluid carrying the drug. Thus, the placement of more than one cannula, which in any case can be called for by the pharmaceutical application, will result in the tailoring of acoustic radiation forces to dramatically enhance such applications.

The waveform to be transmitted is updated and refined after a subsequent transmission of at least one modified waveform pulse by software learning methods performed on received modified waveform pulses at the receivers.

An ultrasound device and software for controlling the flow of material injected into a region of interest of tissue may have and/or at least have:

(i) an array of at least one repositionable ultrasound array of transmitters located outside of the region of interest of the tissue, (ii) output control for the phased transmitters causing pulse trains to be transmitted from the transmitters in the array, (iii) at least one receiver/transmitter receiving the pulse train within the region of interest;

(iv) in some implementations, at least two internal receiver/transmitter transducers to deliver two pulse signals (one from each of the two) to the external array(s) of transducers in order to establish the causal connection between the internal and external transducers as quickly as possible;

(v) a processor capable of executing software for the design of time reversed waveforms for subsequent transmission from the external array, as described above; or (vi) a processor capable of executing software for computational schemes that compute mass flow based on known characteristics of skull and brain tissue, meninges and blood vessels, to simulate the received wave train at a designated point in tissue in the region of interest. In the device an individual patient's image anatomy from three-dimensional radiological imaging may be stored with an information communication link provided from the stored image anatomy to a computer containing a computer algorithm that segments the image anatomy into regions with different acoustical and elastic properties, the software then assigning such acoustical and elastic properties from open database literature, or an individual patient's image anatomy from three-dimensional radiological imaging is stored with an information communication link provided from the stored image anatomy to a computer containing a computer algorithm that segments the image anatomy into regions with different acoustical and elastic properties, the software then assigning each voxel of a brain and skull assigned acoustical and elastic properties derived from said imaging.

The time-reversal approach does assume that the medium (organ in the present preferred context) does not change significantly during the time from the collection of the temporal Green's function data to the time at which the time-reversed signals are sent back into the medium. In a situation where drug perfusion is being performed, it will probably be important to reset (redo) the temporal Green's functions periodically, as they may get stale (that is to say the medium may have changed enough that they need to be updated).

FIG. 1 shows some preferred embodiments of the invention. The ultrasound receivers are within brain parenchyma (as illustrated) and are each contained within a multiple lumen catheter, at least one other lumen being used for infusion of drugs in solution. (The term "drug" will include macromolecules, viruses, cells, and nanoparticles. In general, the active particles that are infused will be such that they cannot effectively cross the blood-brain barrier without the presence of a catheter.) Ultrasound transmitters are placed on the outside of the skull. The figure shows several embodiments within one diagram: (i) The catheters may be just one (e.g. 125) or (ii) multiple (e.g. 125, 126, and possibly others not shown). (iii) The transmitters may be single (e.g. 105) or (iv) multiple (e.g. 105, 106, . . . 109, and possibly others not shown); (v) in addition, a single transmitter is equipped with ancillary frames that allow it to be moved to multiple positions on the skull, such as the positions shown as 106, . . . 109 and possibly others.

The simplest example for application with one catheter infusion port, one receiver and one transmitter, is to design a waveform to prevent backflow (a ubiquitous phenomenon in catheter-based infusions). The backflow phenomenon, which is well known, entails a very thin layer of fluid between the outside wall of catheter and the tissue, which flows up the catheter to a characteristic distance depending on the hydraulic resistance of the tissue, the elastic properties of the tissue, the outside diameter of the catheter, the viscosity of the fluid, and some other parameters. We envision a series of pressure pulses traveling down the (outside) wall of the catheter toward the distal end or tip from which the fluid leaves the catheter to enter the tissue. In order to provide such a series of pulses, one inserts the catheter a short distance into the tissue, sends a pulse through the transmitter, records the pulses at the receiver in the catheter, then advances the catheter an incremental amount, repeats the mentioned process, and so on. Thus one obtains the recorded train of sound at various distances along the track of the final position of catheter. Then we follow the methods of time-reversal acoustics and send the time reversed trains through the transmitter. This will result in the original pulses (to a good approximation) traveling down the shaft of the catheter as desired to effect retardation of the backflow up the shaft of the catheter.

One implementation of time reversal methods is included in the following discussion. For the moment, it will be assumed that the catheter material is sufficiently stiff that it can be rotated after emplacement. This assumption is made for clarity of the conception only and is not necessarily recommended or required. Although one could construct a catheter with a second internal cylinder in close contact with the outer and which could be made to rotate, a preferred approach would be to extend the cylinder from a proximal shielding cannula, image, retract, rotate, extend, and image again as desired. It may be further assumed that at least one transducer (or possibly two, being on the diagonally opposite sides of the catheter opening) is (are) near the end of the catheter. Then, this (these) transducer(s) may be used to localize one (or two) point(s) on the sides of the catheter acoustically. By then 'rotating' the catheter in place and mapping out a set of points along a circular arc just outside the catheter may be effected. With one (two diagonally opposite) transducer(s), this acoustic mapping may be done using a 360 (180) degree rotation of the catheter. The rotation would be done discretely, for example in 8 (or 4 respectively) 45 degree turns. At the conclusion of each small turn, an acoustic signal (ping) will be sent from an active transducer at the catheter if available, or from the external active arrays of transducers (if the transducers at the catheter are not active) that should always be available in the methods being described. This collection of pings and the recorded signals associated with each ping measure/establish the Green's functions between the external arrays and transducer(s) at the catheter walls in each rotated location. Then, focusing back on these locations is performed in the standard way (time-reversal focusing) described elsewhere herein for such focusing. It is particularly desirable to provide a minimum of four points (i.e., four 90 degree turns of the catheter if there is a single transducer, or two 90 degree turns if there are two diagonally opposite transducers) around the catheter walls to do the acoustic beam-forming (also described elsewhere herein) that will produce a ring of higher pressure (acoustic barrier) to discourage backflow of serum along the catheter's external walls. More turns could be used (i.e., eight 45 degree turns), but are not required to produce useful results. Great precision in the catheter rotating process is also not required since all points along the exterior of the catheter are useful points for acoustic barrier focusing. The acoustic wave-forming process itself also does not require high precision either in that knowledge of the precise locations of the transducers is not needed in the signal processing. It is understood that this invention may be used for backflow prevention without the multiple rotation and replacement of the cannulae, since the catheter diameters are small.

Array Processing

The effect described above can be obtained, in fact in a superior way, by multiple arrays of transducers since the timing of these can be more precisely controlled (with greater constructive interference at the desired locations thus producing a larger set of controllable effects) than that of transmission of the time-reversed waveforms through a single array of transmitters.

Thus, both implementations have at least two catheters in the subject organ (brain, prostate, kidney, or other), both of which can receive and record acoustic signals (passive mode), and in the second case also send acoustic signals (active mode). The two catheters should be in the close vicinity of the nodule (or other object or larger region) to which drug delivery is desired. In the simplest and most rapidly implemented case, the catheter transducers are both active. First, at least one catheter transducer (preferably one catheter transducer at a time) emits a pulse, or a short burst of sound; then, the at least one second catheter transducer does the same after a (preferably measured or predetermined) period of time has elapsed so the wave train generated by the first ping has dissipated sufficiently. The pulse waveform itself has a specific design that can be one of many that are approximately localized in both time and frequency, such as Gaussian, wavelets, etc. so that the resulting pulse shape as observed in the time domain is still well-enough localized in time for the particular application. The resulting signals are recorded at all the transducers (being used in passive mode) in the external array. These recorded signals will be referred to as the effective time-domain Green's functions between the sources and receivers. If the externally recorded signals are then time-reversed (first in last out, last in first out) and simultaneously rebroadcast from the external transducer array elements, a strong and well-defined (though usually not perfectly focused) pulse will then appear at the catheter transducers when this procedure is repeated once for each active catheter transducer. It is desirable that the transducers at both catheters use practically the same pulse shape for their individual pings, and also approximately the same amplitude (loudness) for these acoustic signals. Another implementation of the same ideas can be accomplished using catheters having only passive transducers. This approach takes somewhat longer to implement since the temporal Green's functions must then be measured one at a time between the external active/passive array of transducers and the two passive catheter transducers. The time difference is the difference of a factor of 2 for case of active catheter transducers, and a factor of 2 times the total number of transducers in the external array for the case of passive catheter transducers. Since larger arrays will produce more accurate focusing at the spots of interest, the difference will typically be on the order of 100 times slower. Once these temporal Green's functions are known, however, these two methods become exactly the same. So the differences are only in the data collection time, not in the implementation of the wave refocusing, which is just the same in the two approaches.

Another preferred embodiment of this process may be achieved by the generation (or provision) of microbubbles or cavitating bubbles in tissue: this is described below in the description of FIG. 11. These bubbles act as reflective acoustic sources, in that they do not originate acoustic emission or sounds, but reflect sounds in a definable manner when sound waves are directed at them. The operation of the bubbles is that they provide a very good sonic "echo." By time gating the original acoustic signal, you can send a signal from the external transmitter and receive it back from the bubble. The operator then (by knowing the characteristics of the bubble itself, which is available—its resonant frequencies and modes) knows that specific signals came from the bubble.

Sound Wave Synthesis

Returning to FIG. 1, we now describe some other preferred embodiments of the invention. We envisage the placement of other cannulae (e.g., 125 which is not necessarily an infusion catheter as well) into tissue: these must have receivers for the same purposes as outlined above. With the placement of a second cannula, we can now construct a protocol to deliver a specific waveform along the line connecting the two receivers. Equally, we can envisage the placement of up to four transceivers in tissue as being on a sphere, and demand an approximation of the response functions received on this entire sphere. Thus by recording the waveforms received at the respective positions P and Q upon transmission of a pulse from one of the transducers, one can design, by methods and devices described below acoustics, waveforms to induce a pulse anywhere on the sphere, for example. Of course the accuracy of the spatial position of this pulse, as well as its time duration, depend to some extent on the lack of homogeneity of the tissue everywhere, and so will not be perfect. Nevertheless the Approximator described below allows us considerable power in designing such waveforms.

Placement of yet another receiver in a cannula at a third position not in the plane containing the two already placed lines 125 and 126 then allows design for focusing pulses (or indeed any other designed waveforms) anywhere in the parenchymal space, particularly within the triangle defined by the three receivers (approximated as points). Approximations in planar, or spherical, or other regions will allow a variety of applications beyond the prevention of backflow mentioned above. Such applications include enhancing convection of fluid by acoustic streaming along given pathways in parenchymal space. Of course, application of a streaming force in a particular direction (by control of the waveforms) will not always guarantee flow in that direction since the hydraulic resistance of the tissue as well as the anisotropy of such resistance (which is a tensor in general) will determine the actual flow, but flow can be restricted, enhanced or otherwise modified according to the techniques described herein to benefit the delivery or removal of materials within fluid streams in a patient. In other words, the flow direction is the result of the combined interaction of the hydraulic conductivity tensor and the streaming force as a linear motive force. Nevertheless it is clear that designing the streaming force to have certain directions and amplitudes will enhance the controllability of the flow of liquids carrying drugs or other materials within tissue. If the hydraulic resistance were isotropic (not dependent on direction) then the flow would indeed follow the motive force.

The Approximator-Estimator Construction

One aspect of our invention is to be able to construct desired acoustic fields within the medium in question, such as the brain for medical applications, without detailed knowledge of the properties of the medium. For example, individual brains are well known to vary quite a bit amongst themselves or from a particular norm such as an atlas. As noted above, the methods of time reversal acoustics (TRA) allows such focusing at points where receivers are located. A principal inventive claim of this invention is the ability to focus, and to form beam patterns, in regions where there are no receivers. This we shall achieve by methods and devices which we describe under the rubric of Approximator-Estimator construction.

We begin with some terminology within the field of practice of the present technology. If, for example, we observe a signal at one point P and another at Q, and we construct a signal that has the observed values at those points, and some definite values along a path between P and Q, this is called interpolation. If on the other hand, we construct a signal with definite values along the path as just mentioned, but demand only that it be close in some sense to the observed values (the sense in which they are to be close will be made precise later) but not that it reproduce those values at P and Q, then this called an approximation, which we also refer to as Data Matching. We will emphasize such data matching and not interpolations in this invention, for reasons that will be explicated below.

The basis of TRA is the reciprocity of Green's functions. As explained in Reference [1] below, this applies to the frequency-dependent Green function, and so throughout the mathematical development we will be working in frequency space. Of course, we discretize the natural continuous signals, so that to go between frequency space and construction of signal waveforms in time, we use discrete Fourier transforms, which can be implemented fast, as is well known. Thus, some of the basic objects we are manipulating are the spatially dependent impulse response functions, or Green functions, $$G(o,\omega)$$

evaluated at a single frequency $\omega$. The small open circle in the argument of the function indicates we have suppressed other dependences such as the variation in space. These Green functions are of course complex, (i.e., they have real and imaginary parts) but since the acoustic signals in time are real, they of course satisfy $$G(o,\omega)=G^*(o,-\omega) \qquad (1)$$

where the asterisk denotes complex conjugation.

Those skilled in the art know that such frequency transforms are usually windowed (Reference [2]), and that discrete approximations are often better served by wavelet transforms (Reference [3]), which have some nice properties, instead of the older windowed Fourier transforms. We shall take such algorithmic methods and improvements for granted.

The signals we transmit and receive are corrupted by noise. To recover particular parameters (such as the phase) from these is called an estimation problem. This is developed in detail in Reference [4] for time-dependent signals, and in Reference [5] for time and space-dependent signals such as those of interest in the current invention. Detailed development of optimal estimators and so on for general second-order processes are described in these references.

Second order processes are those for means and two point correlations, but not higher order moments, are defined. In setting up estimation problems, as noted below, we require probability distributions and not just the variances or correlations. When we have access only to the second order processes (in addition to the means of course), it is natural to use Gaussian processes, since that captures all information up to second order, and requires nothing further (it is the solution to maximizing entropy of the desired distribution, subject to the constraints that the first and second order statistics are given. Again, there are also non-parametric estimation methods, (which do not require us to specify probability distributions), which are known to those skilled in the art, but we shall not mention these further.)

The problem of approximation is described in a number of references. A classical reference is [6], while somewhat more recent ones are [7] and [8]. Interpolation for deterministic data is also described in references [6] and [7], and for the case of signals in noise in [4]. The reduction to implementable algorithms of the concepts described below can be achieved by the mathematics described in these references. Device diagrams will be given below.

Finally, since our invention applies rather essentially to media that are quite inhomogeneous in their acoustic properties, we provide references, as an example, that describes the fluctuations in acoustic signals in such media (References: [1] Fluid Mechanics. Landau and Lifshitz. Pergamon 1959. Section 74; [2] Digital Filters. R. W. Hamming. Dover 1998; [3] Introduction to Wavelet Analysis. David F. Walnut. Birkhauser 2002; [4] Detection, Estimation, and Modulation Theory. H. L. van Trees. Wiley 2001; [5] Optimum Array Processing. H. L. van Trees. Wiley 2002; [6] Approximation Theory and Methods. M. J. D. Powell. Cambridge University Press 1981; [7] The Mathematics of Learning: dealing with data. Tomaso Poggio and Steve Smale. Notices of the American Mathematical Society, May 2003, pages 537-544; [8] Spline Models for Observational Data. Grace Wahba. Society of Industrial and Applied Mathematics. 1990; and [9] Acoustic wave fluctuations in inhomogeneous media. R. C. Chivers. Journal of Physics D, vol. 13, pages 1997-2003, 1980.

The methods of TRA (time-reversal acoustics) have suggested the importance of receiving the wave-train within tissue or medium of interest (such as the earth) from a transmitter array. We introduce some notation. Let the three-dimensional position of the transmitters be denoted $X_j, j=1, 2, 3, \ldots N$. Let the positions of the receivers be denoted $x_p, l=1, 2, \ldots n$. We also write $r_{p,j}$ to be the distance between the p'th receiver and the j'th transmitter. In general N is much larger than n. It is customary to construct phased arrays with 128 or more elements, while the number of receivers in intracranial applications will be quite restricted for reasons of avoiding unnecessary insult to the brain tissue. However, our description here is not restricted to this situation of N being much larger than n.

It is a capability of the present invention that we are able to direct the ultrasound beam to focus on desired points or over regions away from the specific locations of the receivers. We describe a novel scheme and apparatus for this purpose. We begin the description of the approximator-estimator problem with a very simple example for illustrative purposes only. Suppose in fact we have an ideal point transmitter at the origin, and ideal receivers situated, for example, at a point 2 units of distance away on the Y-axis, and one unit of distance away on the X-axis. Suppose the medium is homogeneous, isotropic and without boundaries. If we can transmit an ideal pulse (a Dirac delta distribution) at the origin, the response at any fixed frequency ω (the display of which we mostly suppress, it being understood) will be the free space spectral Green function $$\frac{e^{i\varpi r_p}}{r_D} \quad (2)$$

where $$\varpi = \frac{\omega}{c}$$

c being the homogeneous speed of sound in the medium, and $r_p$, p=1, 2 being the positions of the two receivers mentioned. Let us focus on the phase alone which is proportional to $r_p$ at a fixed frequency. It is easily seen that if we move along the sector of the parabola shown from the nearer point to the more distant say, at unit speed, then the distance of the point we are at, at any time, will increase linearly with time as well from the nearer to the greater distance. (With the given locations, the parabola we have shown happens to be $y^2-4=-4x$). In other words, forgetting about the amplitude of the wave for now, a linear interpolation of the phases will belong to the wave that reaches a receiver point on this parabola. If the distances to the receivers are much greater than the distance between the receivers, then indeed we may ignore the amplitudes, and find that interpolating the phases will focus the resulting time reversed signal at a point on the connecting arc of the parabola between the foci of each of the original signals. We have therefore been able to interpolate the foci.

Figure 11:
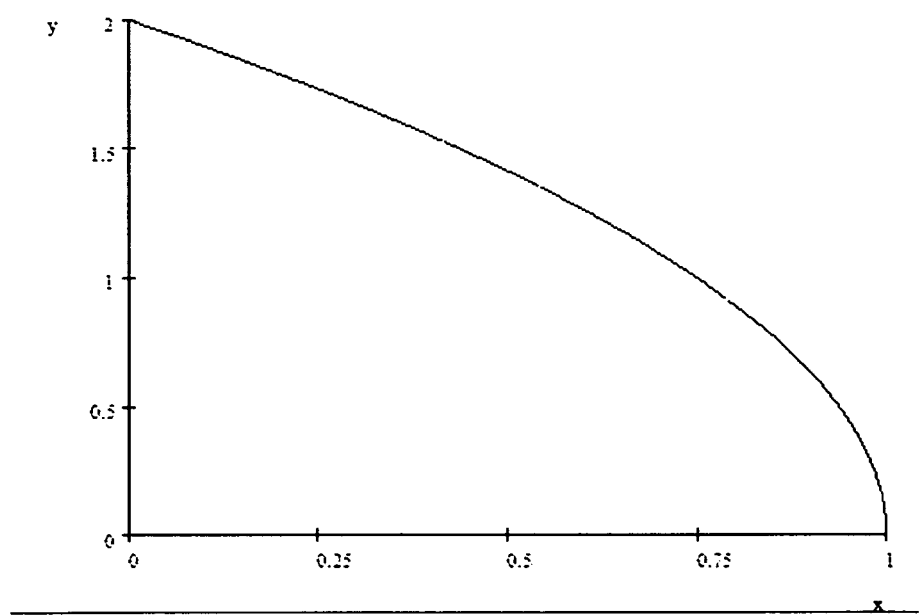
FIG. 11 is a graph of a parabola of foci of receivers according to one embodiment of technology described herein.

The parabola of FIG. 11 in the above example is of course not unique. If all we are demanding is a monotonic interpolation, then if the two points A, B are specified by their respective distances, a and b, from the origin O, we demand that the interpolated point have a distance $$R(w)=wa+(1-w)b \quad (A)$$

for each $0 \leq w \leq 1$. Let us also assume that the distance AB=d. For a fixed value of the weight w, the locus of points specified by the value of r is a circle centered at O. So there is a continuum of curves that interpolate between the 2 points such that the distance from each point along the curve to O monotonically varies from a to b as w varies over its range. One can work the problem backwards. Take the simplest curve as an example: a straight line between the 2 points. Let δ denote the distance, along this straight line, from the point whose distance from O is b, so that δ varies from 0 to d as w varies from 0 to 1. Then r and δ are related through $$r^2 = a^2 + \delta^2 + \frac{\delta}{d}(b^2 - a^2 - d^2) \quad (B)$$

One can then solve eqs. (A) and (B) for w as a function of δ to find a parameterization that satisfies eq. (A). A similar game may be played with curves other than a straight line. We chose a parabola for illustration for the reasons stated above.

This example shows how interpolation might work, and we now generalize this. First, we remark that interpolation, which is defined so that the interpolating function takes the exact values specified at intermediate locations is not of the essence, since for many reasons the values received are not exact, but subject to noise of various kinds. Further, the above example pertained to a perfect medium, in which such constructions are totally unnecessary since we can precompute the desired waveform that will focus at a particular location. In order to discuss the more general case, we first introduce some further notations. The ultrasonic transmitter as well as receive noise is primarily additive thermal noise, (see below) so that we may write for such noise, over the time period for which the oscillator is on, (the symbols are explained below):

$$\varepsilon v(t) = 0 \quad (3)$$

$$\varepsilon v(t)v(s) = \Lambda(t-s) \quad (4)$$

$$\Lambda(\tau) = \int_{-\infty}^{\infty} e^{i\omega\tau} d\lambda(\omega) \quad (5)$$

The first equation of the three immediately above says that the expected value over different realizations (samples taken) of the noise of the transmitter is zero at any particular time. The second says that the noise is stationary because the correlation function depends only on the time separation considered, and not on the particular time chosen. Finally the third equation defines the spectrum of the correlation function: $\lambda$ is called the spectral distribution function and always exists. The form in which the Fourier integral is written is called a Stieltjes integral, but for our practical purposes, we may write $$\frac{d}{d\omega}\lambda(\omega) = f(\omega) \quad (6)$$

where (if the derivative exists!) the function $f$ which is defined in the equation is called the spectral density. Then the Fourier integral above reads like an ordinary (Riemann) integral. In the case of standard thermal noise we can write $$\theta(\omega) = \text{const} \quad (7)$$

where the constant is proportional to the temperature. Obviously in such a case we can only integrate over a finite frequency range (the spectral bandwidth) since otherwise the integral is unbounded. All this has been well known for over half a century, and is described in the above references. We will not spell out the mathematical details to make these descriptions rigorous. However, the methods and apparatus we describe below will carry through for more general noise distributions, including those without a well defined spectral density. Also, as pointed out above, in practice we will always integrate over a spectral window, and so constant spectral densities will cause no problems even if they formally integrate to infinity. The above considerations apply equally to the receiver noise, used below.

For the spectral response at a particular receiver point, from a particular transmitter, for a medium with pre-defined properties, we write $$G_0^{pJ} = \mathcal{N} A e^{iS} \quad (8)$$

where A and S are functions of the receiver and transmitter positions. This dependence is suppressed to make the reading easier. The i in the exponent is of course $\sqrt{-1}$ and not the number identifying a particular receiver. We assume that this $Ae^{iS}$ which is the deterministic spectral Green function is known a priori. As emphasized throughout our invention, we are claiming efficacy in cases where we do not know the medium properties. However, we may choose to begin with our best foot forward, and so we describe one or two embodiments in which we do introduce a starting point for our inventions that can take advantage of what is known of the medium. We describe two methods to arrive at this in the case of brain tissue. In one, we use a brain atlas and we endow each structure in the atlas with specific acoustic properties, so that we can (i) compute the Green function numerically, and (ii) we use one of a variety of image-registration methods to map an individual's brain to the atlas, so that we have the corresponding approximation to the Green function for the individual. In the case of geophysical applications, we proceed similarly, mutatis mutandis. The strength N of the transmitter is assumed to be a known deterministic level plus additive Gaussian noise:

$$N\mathcal{N}(\omega) = N(\omega) + v(\omega) \quad (9)$$

where the noise $v$ has the spectral properties described above.

Continuing with the illustrative application for the brain, we write the true response function for the individual at the receiver as $$G^{pJ} = G_0^{pJ} e^\alpha e^{i\beta} \quad (10)$$

Now, $\alpha$, $\beta$ are not only functions of the positions as described above, they also vary according to the particular realization of the medium (e.g., the particular brain). To make this dependence on the sample explicit we can write $\alpha = \alpha(\sigma)$ where $\sigma$ is the particular sample considered. Due to the assumptions above that $G_0$ represents a nominal or averaged medium, we have that the average over samples of $\alpha$ or $\beta$ is zero. We write this as $$\epsilon_\sigma \alpha = 0 \quad (11)$$

and similarly for $\beta$. Note that these samples are in a completely different space than the noise fluctuations we considered above. These variations with samples are due to fluctuations of elastic or poroelastic moduli as the case may be and of the density. We then also write $$\langle \alpha^2 \rangle, \langle \beta^2 \rangle \quad (12)$$

for the mean square fluctuations of these quantities. For normal acoustic waves in an inhomogeneous medium these mean square deviations can be written in terms of the variance and correlation functions of the density and compressibility inhomogeneities. This was worked out very early on for compressibility variations, which are also the most important for the medical applications envisaged in this patent, by Russian (then Soviet) investigators such as Rytov and Chernov centered in time around the second World War. They were then improved upon to allow density variations as well. Explicit formulas may be obtained from Reference [7] for example. We have defined the true response functions in the absence of receiver noise, though we have allowed for transmitter noise. We can adopt an additive noise model for the receiver as well, and write that the received signal as a function of frequency (i.e., the spectrum of the received signal) is then $$R = T(\omega)(G^{pJ} + \eta) \quad (13)$$

where $T(\omega)$ is the transfer function of the receiver with finite spectral width and $\eta$ is the noise spectrum, which we can model as accurately as the data allows, or use again a simple thermal noise model as above.

We can now define the Data Matching or the Approximator-Estimator problem that is a key component of this invention. We shall define it only for the phase fluctuations $\beta$, since its definition for $\alpha$ can be copied from this, mutatis mutandis. We have chosen the phase since that is the more important quantity that determines the effectiveness of the TRA.

Define $$\hat{\beta}(x,X) \quad (14)$$

to be the Response Approximator. We shall also use the same word to describe $$\hat{\beta}^J(x) \quad (15)$$

where we fix the position of the transmitter J and are only interested in the variation with position in the medium. We now further simplify the notation to write $$\hat{\beta}(x) \quad (16)$$

where the transmitter location is simply suppressed. This is typographically simpler, but it should be understood that the following considerations will involve the transmitter location and characteristics, and can also be carried out for the more complex function of two sets of positions above.

DEFINITION

The response approximator is constructed from an estimator of the phases at each point $$\hat{\beta}^i \approx \beta^i \quad (17)$$

and is an approximator of the phases $$\hat{\beta}(x=x_i) \approx \hat{\beta}^i \quad (18)$$

We make this definition more precise. Again for mathematical simplicity, we will assume that the noise distributions have a density. If we are given only the power spectra of the noise, (as we have described above), then we can assume a second order noise process, or a correlated Gaussian probability density. Let $p(R=r|\beta^p)$ be the probability density for the received signal at fixed frequency $\omega$ to be r given the phase to be $\beta^p$. The estimator problem begins with a desire to construct the estimator $\hat{\beta}^p$ to be close to $\beta^p$. The estimator of course will and should depend on the received signal r but not of course on the unknown parameter it is attempting to estimate. We can choose a least square norm (although other norms such as the absolute value or $L^1$ norm may be preferable in certain circumstances; often the convergence with number of samples is faster, though the computational cost is usually greater). We continue the description with the mean square or $L^2$ norm. Then the best estimator is one which minimizes $$\int dr\, p(r|\beta^p)(\hat{\beta}^p - \beta^p)^2 \quad (19)$$

If we don't add to this requirement, the problem may be ill-posed, since the solution of the above problem by itself is simply $\hat{\beta}^p = \beta^p$, which is of course unknown so that's no help. One common additional restriction to make the problem well-posed is to demand that the estimator is unbiased $$\int dr\, p(r|\beta^p)\hat{\beta}^p(r) = \beta^p \quad (20)$$

(recall that the estimator is a function of the signal r, as stated above). Another requirement, which may be more natural for our purposes is for example to demand that the estimator have minimum least square error, when averaged over a range of variation of the parameters $\beta^i$, due for example to the variation of different brains in the medical example. In other words we find $\hat{\beta}^i(r)$ such that $$\int d\beta^i \omega(\beta^i) \int dr\, p(r|\beta^i)(\hat{\beta}^i(r) - \beta^i)^2 \quad (21)$$

is minimized where the values of the weights w are all non-negative, and for convenience integrate to unity (so they define a probability density in the range of variation of the true phases. In fact the estimator for the above problem is immediate (by differentiating with respect to the function $\hat{\beta}^i(r)$):

$$\hat{\beta}^i(r) = \frac{\int d\beta^i \beta^i \omega(\beta^i) p(r|\beta^i)}{\int d\beta^i \omega(\beta^i) p(r|\beta^i)} \quad (22)$$

(We remark that the condition of unbiasedness in the statistical case corresponds to an interpolation in the deterministic case while the general least squares corresponds to an approximator with the same loss function.) Thus we have given examples of the estimation problem, its posing, and possible solutions. It should be understood that more suitable loss functions may well be proposed. If for example, we choose the absolute value instead of mean square, we cannot write down an analytic solution, but have to rely upon solving a linear programming problem. Nothing in the above description should be construed as restricting ourselves to particular loss functions or particular noise models, though the ones described are the most convenient and simplest. The detailed construction of such estimators based on power spectra considerations will utilize heavily the classical mathematical methods of Kolmogorov and Wiener who developed the theory of interpolation, estimation, and smoothing of second order processes during the years of the second World War. It extension to array processing was worked out in subsequent years, see for example the textbook Ref [3] above.

We have indicated how we can make one portion of the definition precise, namely the estimation problem. The other portion, namely the approximation or data matching problem is quite simple to make precise as well. In the estimation problem we restricted ourselves to the particular spatial points where the receivers were located. For the data matching problem we focus on the spatial variation of the estimator, i.e., $\hat{\beta}(x)$. Having estimated this function at particular points we demand that we obtain a function of space (and frequency, of course) that is obtained from some class of functions, so that a suitable measure of distance of $\hat{\beta}(x)$ from $\hat{\beta}^i$ is minimized. As is well known, if we choose the distance function to be $$\max_p |\hat{\beta}(x) - \hat{\beta}^p|,$$

we may by restricting the class of functions, obtain an interpolation. However, owing to the errors in $\hat{\beta}^p$, we may also select the class of functions and distance measure to obtain an approximation, as mentioned above. Several methods for doing so are described in the References [5] and [6] above, and many more possibilities can be envisaged by those skilled in the art.

We now, importantly, generalize this to the case where the job is to construct $\hat{\beta}(x, X)$ from the observed signals, via $\hat{\beta}^{p,J}$. We shall adopt the point of view that the receivers, identified by lower case Latin letters such as p, can also transmit. As explained in the text, this is helpful from the point of view of real-time signal processing, since then a signal transmitted from p can be simultaneously received by all the J's. We emphasize that this is only for convenience, and that all the quantities described below can be constructed just as well by having no transmitters within the medium at the cost of serially recording the signals from each transmitter, and using reciprocity as before.

We generalize the construction of the estimators $\hat{\beta}^{p,J}$ from those for the estimators $\hat{\beta}^p$ by using essentially the same procedure as above. We require a multivariate generalization of the probability distributions above, so that we now write $p(r|\beta^p)$ where the list $r=(r^{p1}, r^{p2}, \ldots r^{pN})$ being the signals received at each of the external transceivers from the internal one at p. (As stated above, if the internal device is a receiver, then this list has to be constructed in serial fashion by receiving the signals at p one by one from each external transceiver. This is a detail of implementation.) This similarly holds for $\beta^p$. Now an important distinction from the univariate case is that the spatial correlation functions are involved. Essentially all the external transceivers respond to the signal. In the simplest case, this will involve a time delay corresponding to arrival of a wavefront at each of these transceivers, but due to the complexity of the brain tissue environment, as well as reverberations within the skull, such a simple model will emphatically not hold in the applications of interest here. Nevertheless the correlation spectrum can be measured, and this will then affect the solution of the estimation problem. For example, one interesting and potentially important consequence is that an estimate of $\hat{\beta}^{p,J}$ for given p, J will be affected by the signals received at $J \neq J'$. We may expect that if an external transceiver is very close to the given internal one, it can affect the estimate of the response function between the internal one and a more distant external transceiver. Thus setting up the problem as a noise model allows us to weight strong and reliable signals appropriately. The final step in the construction is now the Approximator. We can now use loss functions that again weight the reliability of the point estimators $\hat{\beta}^{p,J}$ (for this we not only have to construct these estimators but also evaluate their noise characteristics which can be done with known mathematics) so that our approximator is the more reliable according to the reliability of the point estimates.

Figure 8:
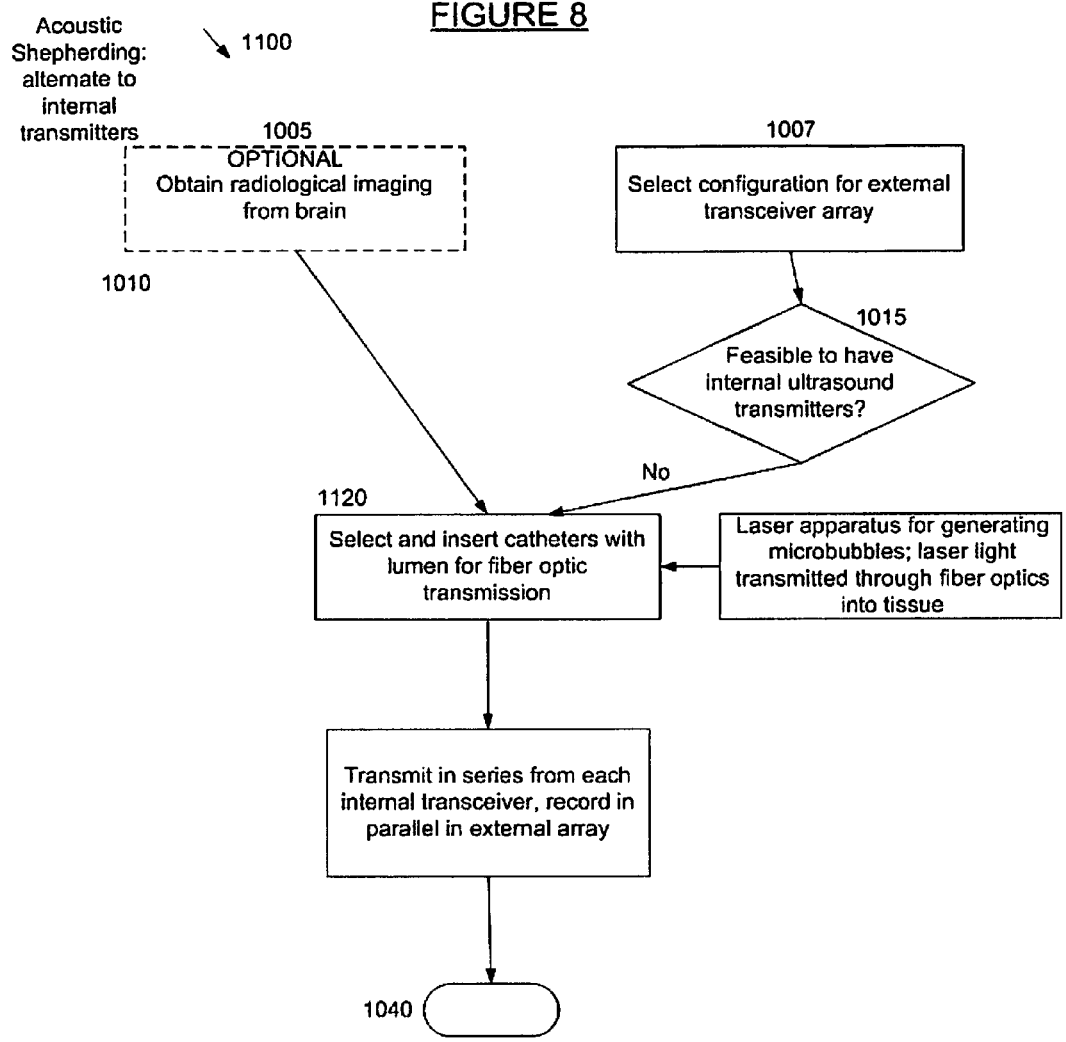
FIG. 8 shows a flow chart of a specific process within the generic concepts according to the present invention.
Figure 8A:
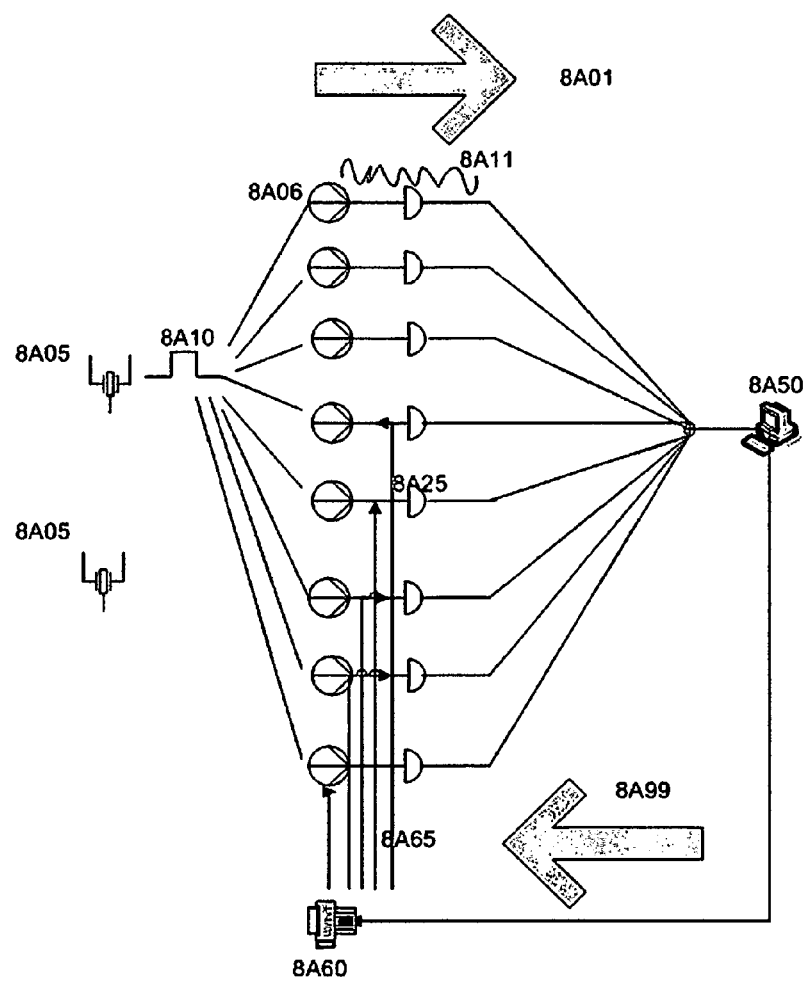
FIG. 8A shows the construction of the Approximator-Estimator that allows beam forming for desired applications which require considerations beyond focusing at the locations of internal receivers of transceivers.

We summarize the apparatus for the construction of the Approximator in FIG. 8A. This figure shows the internal transceiver on the extreme left (8A05). As discussed above, the embodiment shown in this figure where the internal transducer can transmit is not a limitation on the invention, since the reciprocity of the impulse response allows us to accomplish the same goals by serially transmitting from the external transceivers which are always required to be function both as transmitters and receivers. We have shown the more convenient and time-effective embodiment in the diagram. 8A10 shows a pulse, which we assume for the moment is the waveform desired at some internal location. This also should not be construed as a limitation since if different waveforms are desired, then they can be either transmitted or reconstructed from the responses to pulsed waveforms by known transform methods. To continue with the figure, this pulse is received by all the external transceivers in parallel (8A06 shows one of a bank of such transducers in an array or in an array of arrays). However, the waveform received is no longer a pulse but is distorted by the medium and received as multiple reflections off the containing skull, etc. and so is shown in graphic form by 8A11. Different external transceivers in the array will receive somewhat different waveforms (not shown). The received signals pass through A/D (analog-to-digital) converters, one of which is indicated in 8A25, and are fed into either a general purpose computer (8A50) or special purpose digital signal processing chips which includes spectral (Fourier) transforms. This process of analysis of waveforms is indicated by the process arrow 8A01 running from left to right. After the approximator-estimator construction is performed in software, the arrow 8A99 indicates the process from right to left which consists of excitation (and so perhaps involving a digital to analog conversion) of the external transceivers to produce a time-reversed signal (or more generally, when a waveform is desired outside of the location of the internal transceivers, to produce a synthesized signal that is obtained by a process such as described in the preceding text. A further preferred embodiment of this invention is the repositioning of the external transceiver array or arrays by a servomotor (8A60) which is connected to the array (8A65) and can be instructed by the computer and human operator to reposition the transmitters for more efficacious application of the streaming force. This can be particularly important when a bolus is being guided through channels over longer distances. Geophysical and environmental applications may particularly benefit from this.

SUMMARY

We have shown how our Approximator-Estimator construction may be enabled and allow us to develop beam formation patterns that can focus at points or over regions away from the location of the internal receivers or transceivers. For the final application, we simply use the $\hat{\beta}(x, X)$ that the above described approximator yields to design the transmission waveform according to known methods in phased array technology such as described in ref [5] or other treatises specialized to medical or other acoustic processing. Also, the digital processing acts upon a signal, originally in analog form, which has been both sampled and quantized (finite precision of the arithmetic), and the use of digital filters and windowing to optimize the noise characteristics of the transformed waveform is presupposed as applying to the invention, according to the practice of those skilled in the art. By a similar token, the technology used to construct the transducers and arrays can vary according to the application, the medical ones lending themselves to utilizing micromachined ultrasonic transducer construction, while the more robust environmental ones can call for bulk equipment.

CONCLUSION

It remains to state one additional conclusion. We expect the Approximator to be used in altering the technological design, and more pertinently for real-time use, in dynamically altering the position of the external transceivers to more optimally form the desired focal regions for the applications of interest. For this purpose, the reduction of the Approximator construction to user-friendly software that can run fast is necessary. Such methods of reducing well defined mathematics and mathematical algorithms to software are of course available to skilled practitioners. We will then be able to redesign the hardware and the design of the geometry of the external phased array, as well as suggest new device positioning for the internal receivers, based on initial in-vivo testing; and alter the position of the external transceivers based on results obtained during the clinical use of the devices. We are emphasizing the external devices because they will be most amenable to re-positioning. The approach would work as well for the internal devices, but at least in patient care, we do not expect to have the luxury of repositioning these to any significant extent. Non-medical applications, such as the environmental or the geophysical, can be exploited more easily in this regard.

The waveform design step described above produces a focused spot of sound at a points not located at either the at least two catheter transducers. A variety of mathematical methods is available other than those detailed above to those skilled in the art. Both non-parametric methods (such as Empirical Risk Minimization) as well as parametric methods may be used. Also, as stated above, and as those practiced in the art are aware, one can choose other figures of merit, such as the maximum error (to within a tolerance) which may result in better stability of the interpolation, but at the cost of having to run a linear programming solution to obtain the estimator. Similarly, other methods may demand quadratic programming. Extensions to the more complex cases needed for applications, and to substitute other interpolation schemes including interpolation on spherical surfaces, and other geometric objects can be envisaged.

Thus, soundwave design can be accomplished using a combination of time-reversal data collection, frequency domain data processing involving the geometric mean of the empirical Green's functions, and subsequent rebroadcasting of the signals from the external array in the reversed-time domain. Caveats that should always be kept in mind include: if the medium is heterogeneous in space (the usual case), the rebroadcast signal may be only weakly received at the original location. The focus at this location may be either better or worse than normally expected (when measuring against the Rayleigh criterion), since spatial heterogeneity can actually improve the focus—due to the presence of greater angular diversity in the received signals, while simultaneously creating extra sources of amplitude loss. If there is significant time dependence in the medium properties, then these response functions may have to be re-acquired, so that the waveform design uses the current properties of the medium, rather than ones that obtained at an earlier time and that may have changed. For the main types of applications envisioned by the inventors (to biomedical problems such as drug perfusion problems in brain, prostate, or other tissue and organs), there is no anticipation from the teachings in this art that temporal degradation would be a major source of difficulty with the application of the methods outlined herein.

One way of characterizing this method is as a method of providing a focused soundwave using soundwave design procedures comprising:

providing signals from at least two positioned sound sources having known positions in three-dimensional space and known pulse shape in a frequency domain, receiving signals at a transceiver within a target volume, producing spots of soundwave concentration at particular points in the target volume not at the positions of the receivers which are in the target volume, combining data related to received signals as well as the positions or external and internal transceivers by the methods of estimation and approximation theory to determine at least one value for transmission from each of the positioned sound sources.

Although specific materials, apparatus, formulae and the like are used in the above descriptions to enable one skilled in the art, those specifics should be considered as examples within a generic framework that has been more broadly enabled than the scope of the examples themselves.

Figure 2:
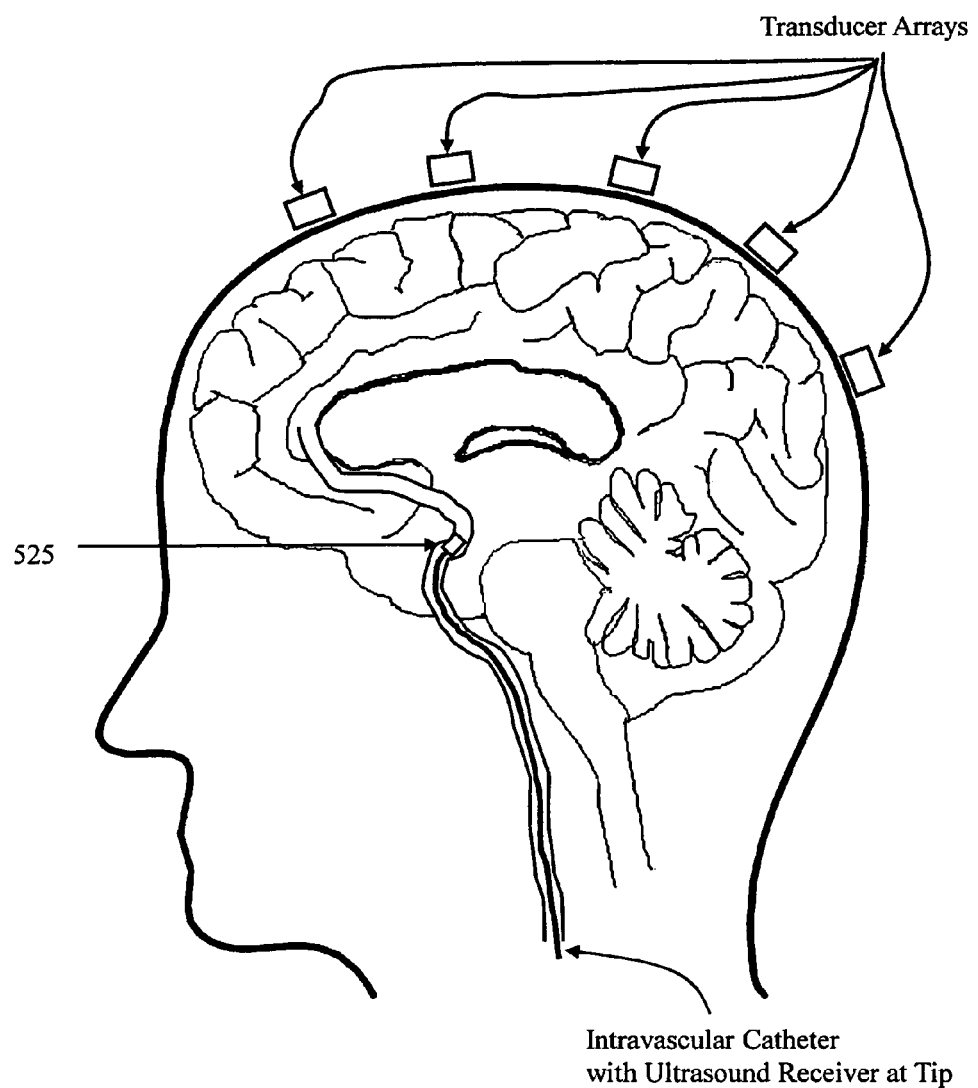
FIG. 2 shows an endovascular embodiment of technology within the scope of the generic invention.

FIG. 2 shows an endovascular embodiment of technology within the scope of the generic invention. The catheter, which may be a microcatheter, has one or more receivers along its length. It is inserted into blood vessels in the brain. In the case of one receiver at its distal end (525), such a receiver must be positioned as close to the region of brain parenchyma where the drug is to be administered. In the case of two receivers, an aim would be to deliver this therapy to a region of the brain distributed radially around the line (or proximate to the line) joining the two receivers as an axis. The therapy is then delivered endovascularly, preferably by the catheter, or by an injection, and the invention is used to focus ultrasound in the region of the vessel at the receiver or between the receivers. The sonoporation that results from the focusing of the sound is expected to increase the blood brain barrier permeability and allow increased efflux of drug into brain parenchyma for therapeutic effectiveness. The advantage of our invention is that transmitter technology and electronics need not be inserted into the blood vessels, resulting in a significant advantage in cost in the single-use catheter, as well as reducing the requirements for safety due to the significant reduction in power in the electronics that is inserted into the body. We may envisage further increasing the effectiveness of the sonication by providing streaming or sonic guidance to further distribute the therapeutic particles into the tissue. In addition, the level of sonoporation (power, frequency, etc.) may be optimized by incorporating the known pharmacokinetics of the therapeutic molecule so that a desired level of penetration into tissue may be effected.

It is understood that the receiver need not be inserted into the blood vessels, but may be placed in tissue in a region of the brain targeted for perfusion by the drug, so that blood vessels nearby may be sonoporated by this technique. However, it could legitimately be pointed out that having a catheter or cannula within tissue could equally be exploited to deliver the drug, and hence opening the blood-brain barrier would be unnecessary in such an intervention. Nevertheless, we mention this possibility as well.

A preferred embodiment of this technology which overcomes the objection stated in the previous paragraph would be in conjunction with microcatheters introduced into the venous system to reach close to almost any desired position in brain parenchyma. The vein there may then be punctured, and a systemically administered agent would then have privileged access to that region of parenchyma adjacent to the punctured vein. Ultrasound focus could be provided by the afore-described time reversal techniques to distribute the agent favorably in the brain.

FIG. 2A shows an embodiment that can guide a bolus through the vasculature by the use of high contrast materials, the echoes from which can guide the time reversal ultrasound to continually nudge the bolus through the vasculature to a desired location. We mention that the streaming force on a fluid in a tube such as a blood vessel has distinct and different characteristics than that for streaming through the microchannels of a porous medium, but the time reversal procedure will work similarly. A repositionable array (2A10) of transceivers is used in conjunction with contrast enhancing bubbles which encapsulate the therapeutic agents (2A50). The process of time reversal focus described is used to develop a waveform to guide the bolus to a desired location, for example as indicated by the arrow 2A99. When the streaming has achieved the desired positioning the therapy may be released into the tissue by a number of other processes, such as sonoporation described in the literature. It is understood that the repositioning of the transducer array is not a strict requirement since if an array is available to cover the entire length and width of the path of the bolus, the repositioning can be dispensed with. In practical use, we envisage that repositioning will be called for.

Figure 3:
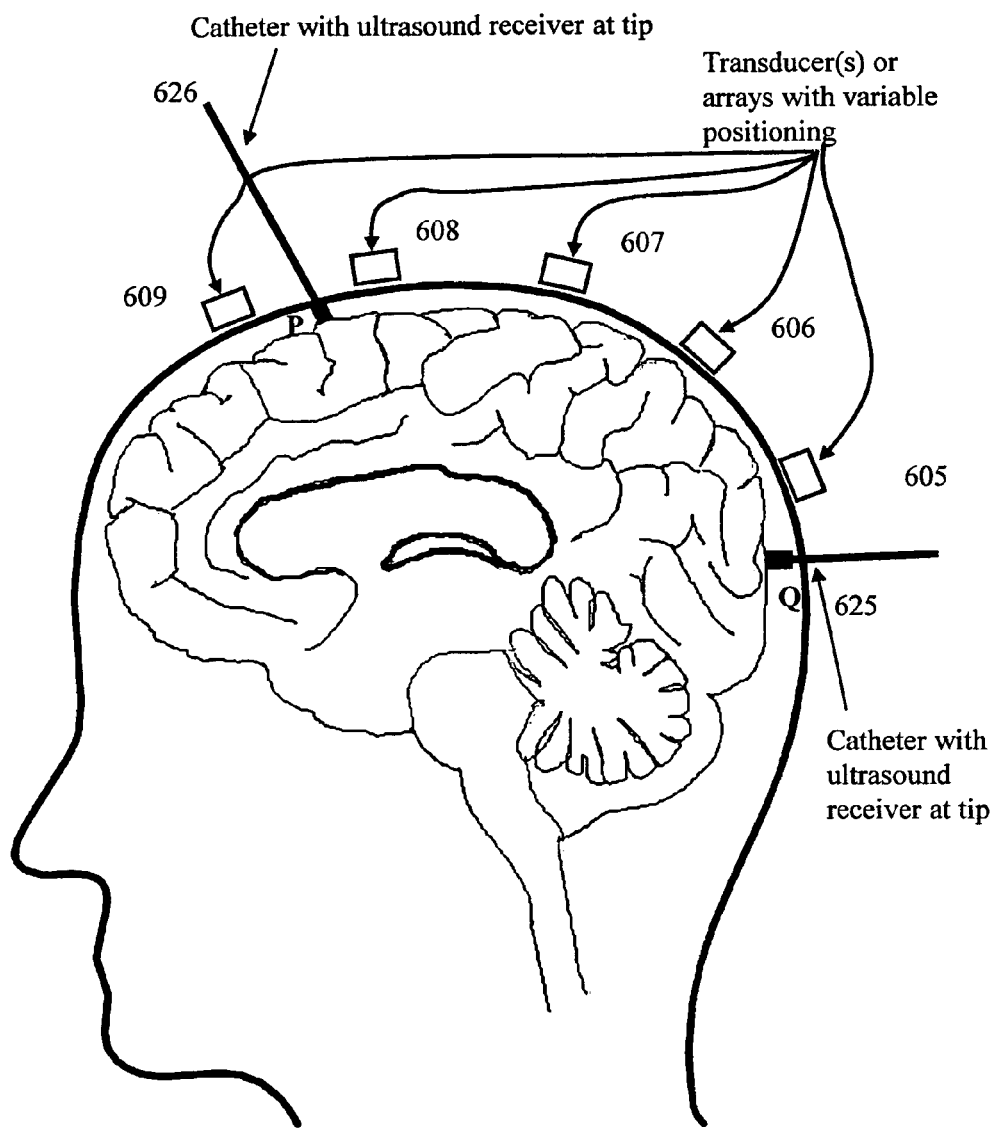
FIG. 3 shows an application of the technology within the generic scope of the invention to intrathecal delivery where an objective is to enhance delivery of drug or therapeutic particles into cortical tissue.

FIG. 3 shows an application of the technology within the generic scope of the invention to intrathecal delivery. Here, the invention performs two separate functions. The intent is to get drug or therapeutic particles into cortical tissue. The cortex is enveloped in a thin layer of cells comprising the pia mater. The cerebrospinal fluid (CSF) flows in the sub-arachnoid space between the pia and the dura mater. Intrathecal delivery involves injection of therapy into the CSF, usually in the spinal column, though it can also be performed subdurally. However, such a procedure would be very unlikely to deliver the drug into the cortex for two reasons: first the flow of the CSF will more likely move the therapy away from the intended cortical targets to the CSF drainage areas, and secondly, the pia itself is a barrier to the entry of especially the larger molecules, as the BBB is (though the pial junctions are not as tight). One application of the present technology may be aimed at overcoming both these difficulties. A focus of the ultrasound will be near the site of the intrathecal delivery (625). A phased delivery of ultrasound will direct the flow of the therapy to near the site of the intended cortical penetration (626). A different beam formation will then attempt sonoporation to reversibly open the pial barrier to allow and direct entry into the cortical matter. The methods of beam forming and of time reversal to focus and phase the ultrasound will be as described before.

The method can also be practiced as an application to the oil industry, where a common problem is that certain oil reservoirs have known fluids that are stuck underground, and it would be helpful to shake them up a bit and get them moving again. Similarly in the environmental community where certain contaminants are present underground, it would be advantageous to be able to shake certain contaminants loose and control the direction in which they flow so they do flow to the desired contaminant collection point.

Figure 4:
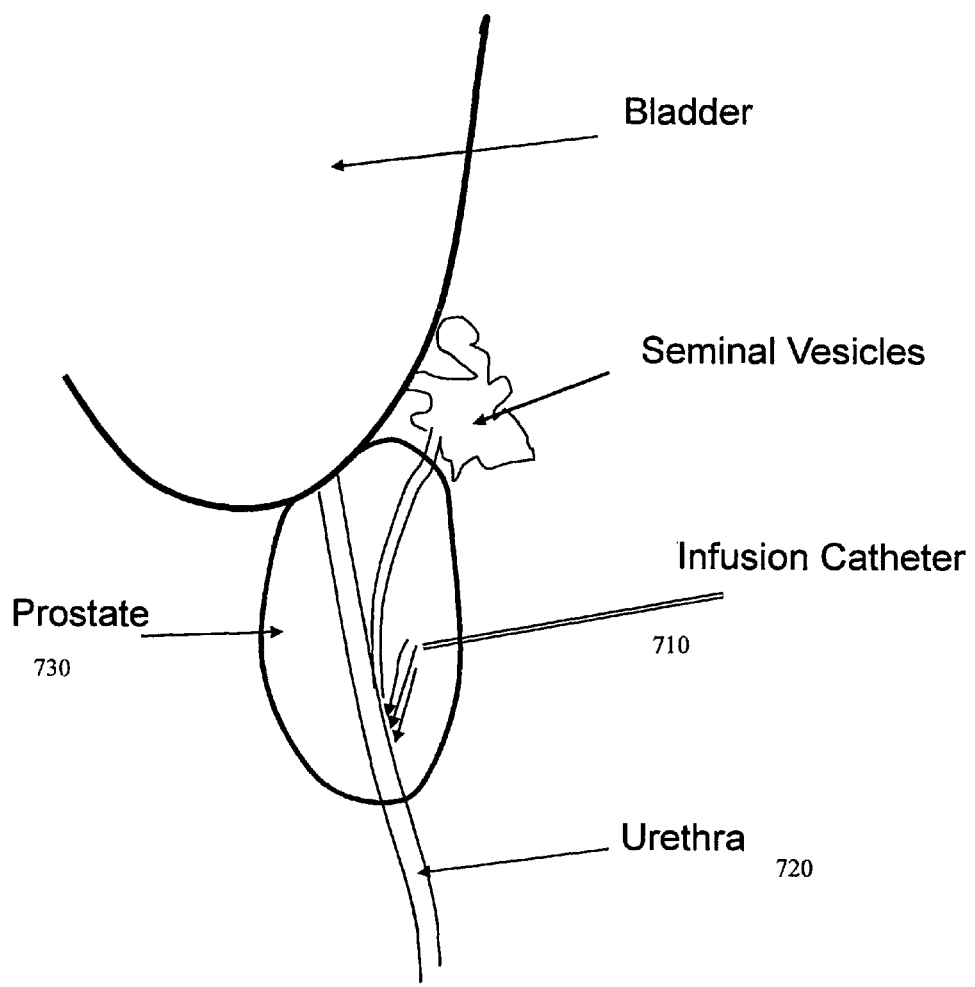
FIG. 4 shows a schematic representation of problems faced when infusion of therapeutic solutions into the prostate gland is attempted.
Figure 5:
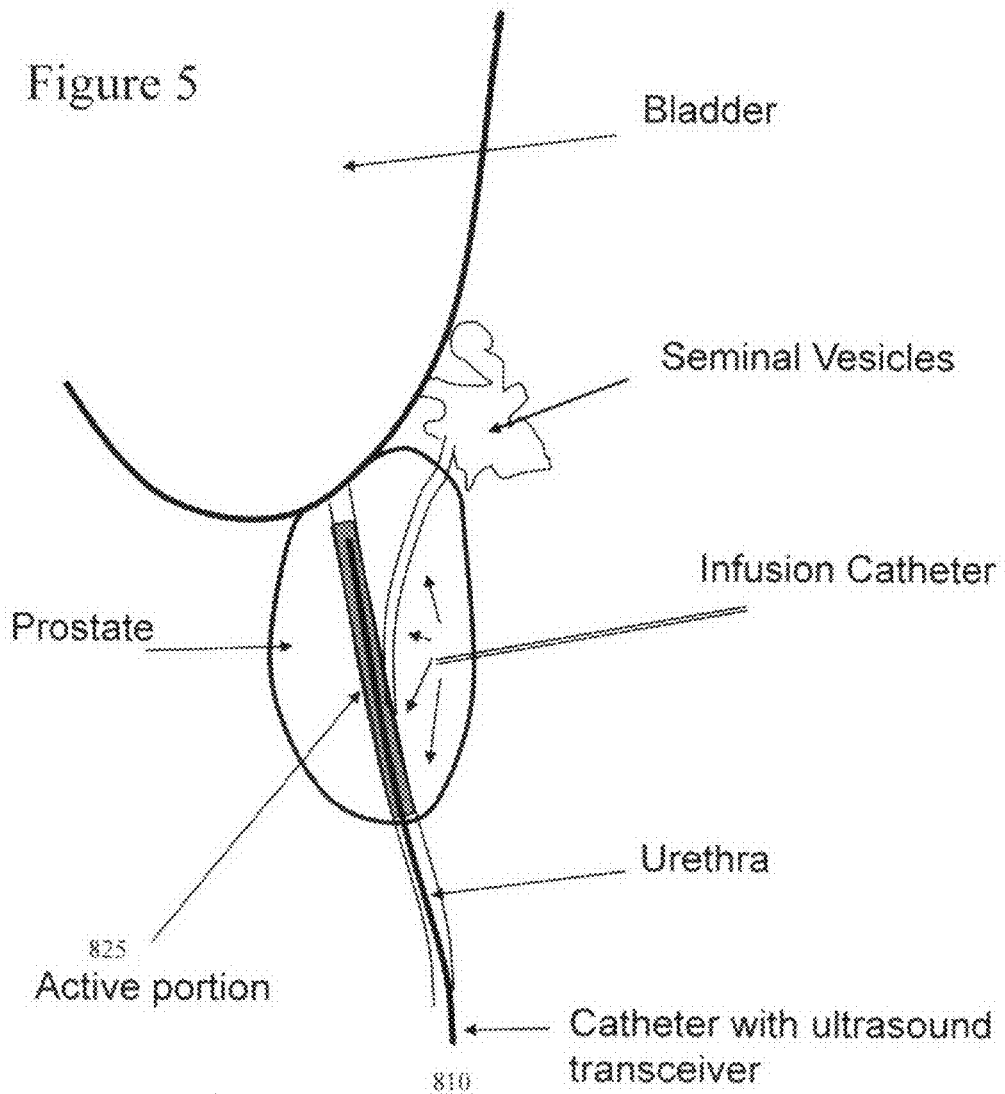
FIG. 5 shows a schematic representation of one practice of the present technology on a prostate gland.
Figure 6:
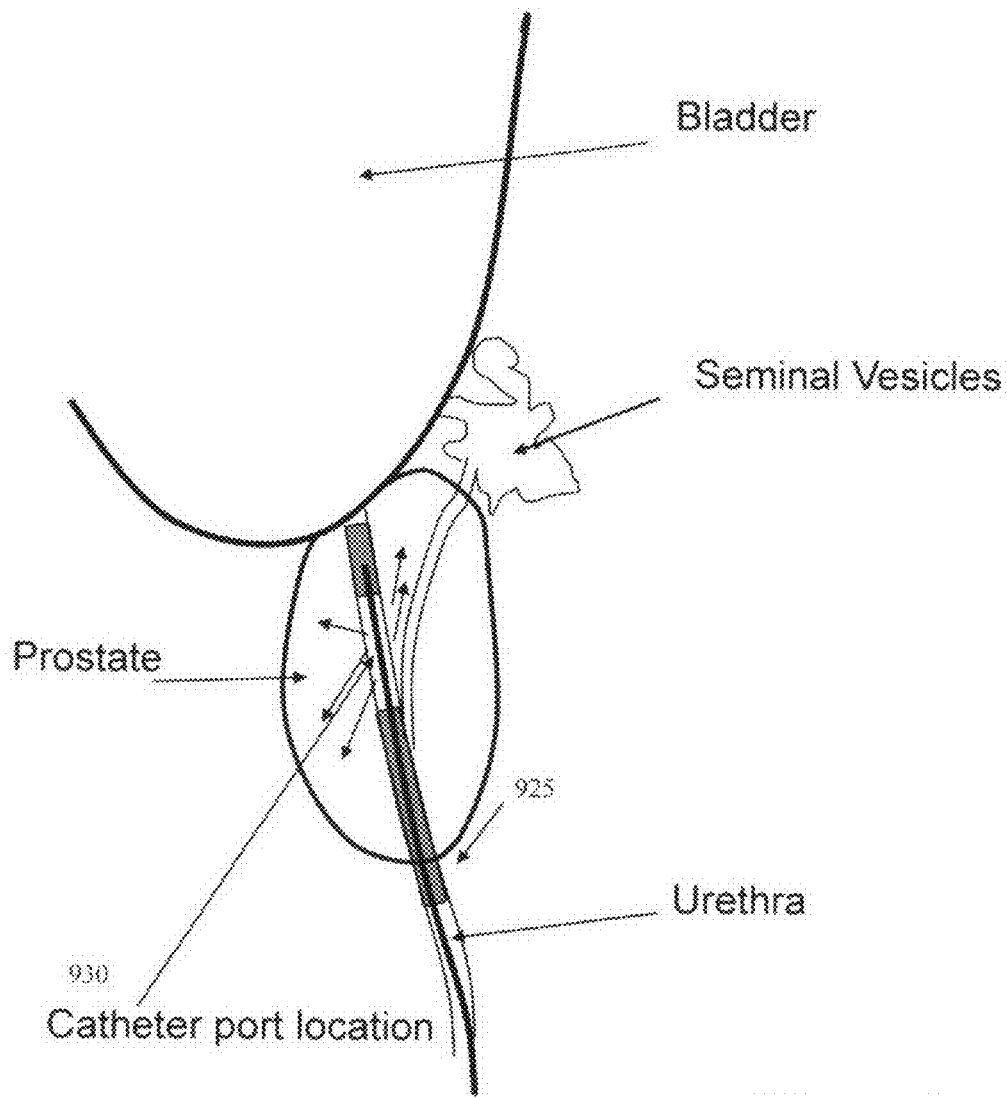
FIG. 6 shows a schematic representation of another practice of the present technology on a prostate gland.
Figure 7:
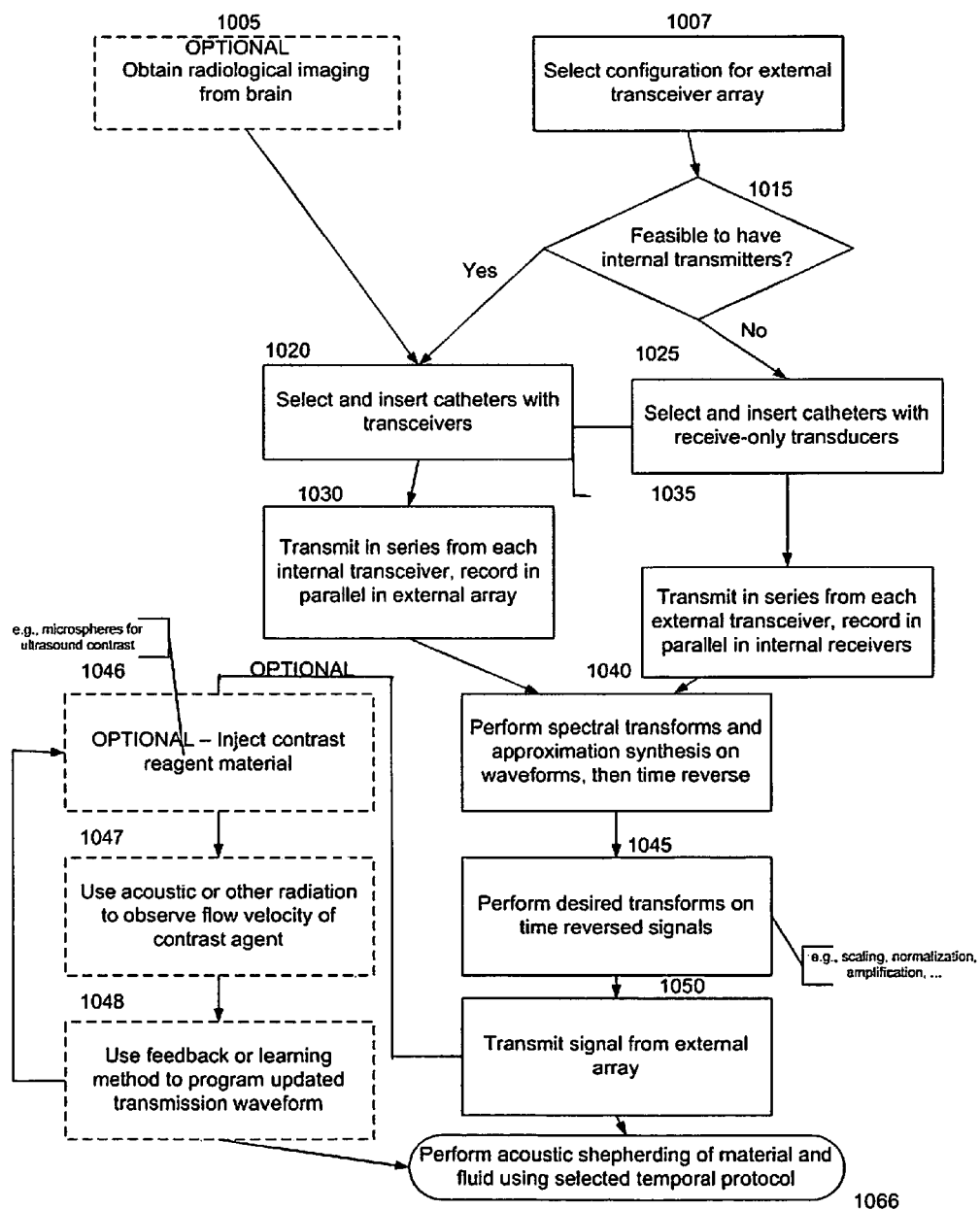
FIG. 7 shows a flow chart of a specific process within the generic concepts according to the present invention.

FIGS. 4-6 show schematic representations that envisage an embodiment of the invention for prostate therapy wherein fluids are infused intraparenchymally into the prostate. As shown in FIG. 7, when drug is infused from one or several injection sites within the prostate, (only one of which is shown in 710) a problem to avoid is that the fluid flows into ducts which lead into the prostatic urethra 720. The fluid-filled ducts are a low pressure sink for fluid flow and this makes it difficult to obtain a uniform distribution of the infusate or the drug carried therein. One embodiment of the present generic technology of the present invention is to introduce a catheter with ultrasound transceiver, or two transceivers, through the urethra into the prostate. Monitoring of this process by MR imaging or other means is preferred. The waveform desired at the location of the receiver within the volume of prostatic tissue is then fed into the transmitter array which is located outside. The methods of time reversal focusing as outlined above are then used to direct a streaming force away from the prostatic urethra into the tissue. This will force the infused drug away from the urethra and allow it to distribute more evenly within the prostate.

FIG. 7 shows a flow chart of a specific process within the generic concepts according to the present invention. There is a first optional step 1005 in which a radiological (or other format) image is taken of the general locus of the planned treatment, here indicated as the brain. To assure a beneficial image 1007, the user selects or designs a configuration for the external transceiver array to be used in transmitting sonogram pulses and signals into the area of interest of the patient. In step 1015, it is determined whether it is feasible to use internal transmitters in providing the signal. Medical technologists would be aware of the basis of selection of such parameters, such as ease of access, potential for damage from insertion, removal or proximal signals, and the like. If the answer is yes, in next step 1020 one selects and inserts catheters with transceivers into the appropriate area of the patient. A next step would include transmitting, most likely in series, but in a designed pattern is also possible, pulses or transmissions from each internal transceiver. The signals are then recorded in parallel in the external array. At this point after using internal transceivers, spectral transforms and transformations on waveforms would be performed and time reversed 1040.

If the answer in step 1015 was no, then the procedure would move to alternative step 1025 one selects and inserts catheters with transceivers into the appropriate area of the patient. A next step would include transmitting, most likely in series, but in a designed pattern is also possible, pulses or transmissions from each internal transceiver. The signals are then recorded in parallel in the external array. At this point after using internal transceivers, spectral transforms and transformations on waveforms would be performed and time reversed 1040.

In each case, after step 1040, one could then perform in step 1045 desired transforms on the desired time-reversed signals, such as scaling, normalization, amplification and the like. Once the signal data have been provided in a form designed to have the local sonication effect within the patient in the area that has been evaluated, an actual procedure 1050 can be performed where the operator transmits the altered signal towards the target area to have the effect desired from the adjusted or altered signal, such as performing acoustic shepherding of material and or fluid.

The method can be improved with the use of contrast agents to permit visualizing the effects of Acoustic Shepherding. For example, FDA approved microbubbles or spheres may be co-infused with the therapeutic agent, or at the beginning of the infusion with the therapeutic agent as shown in step 1046. A transmit waveform of a frequency resonant with the microspheres, with time-gated reception at the external array will provide information about the success of the shepherding. Thus the movement of the particles is observed 1047 by acoustic or other radiation, a frequency resonant with the microspheres, with time-gated reception at the external array will provide information about the success of the shepherding. Thus the movement of the particles is observed 1047 by acoustic or other radiation, detecting or measuring flow velocity of contrast agent. Feedback 1048 is then used to evaluate, appreciate or analyze and learn about movement of the injected material. Once such feedback is obtained, the method can be augmented with learning methods such as neural network methods, genetic algorithms, least square estimations, density estimators, and support vector machines.

It is understood that microspheres may be infeasibly large for several applications such as drug transport through the interstitium of gray matter in the brain. In such a case, nanospheres with sufficient contrast may be used. Gold and other materials inert or non-interacting with live tissue may be used as appropriate.

FIG. 8 illustrates that sound sources inside the brain (e.g., when attached near the tips of the catheters or other placement systems) could either be similar to those in the external transducer array (for example, piezoelectric transducers) or they could be of a different type of external transducer array, making use of optical fibers to send light pulses that will heat the fluids locally and create sound sources in the form of cavitating bubbles in the liquid. Such methods for creating cavitating bubbles can follow the disclosure of U.S. Patent Application Publication 2004/0054357, published Mar. 18, 2004, titled "Method and system to create and acoustically manipulate a microbubble" by Matthew O'Donnell. The feasibility of this approach for creating microbubbles was demonstrated in the publication "Mapping elasticity in human lenses using bubble-based acoustic radiation force" by Kyle W. Hollman, Matthew O'Donnell and Todd N. Erpelding, published in *Experimental Eye Research*. Vol. 85, pp 890-893 (2007).

FIG. 9 is a flow chart indicating one format of an soundwave design process comprising some of the steps described in detail above. In the example provided in this Figure, the received waveforms have been collected by the process described in FIG. 10 (or FIG. 11), comprising the set we denote $G_{IE}$, where I=1, 2, ... J count the internal transducers, and E=1, 2, ... N count the external transducers in one or more arrays. These waveforms are collected over a long enough time as appropriate such as wavelet transforms), also as previously described. A data matching of the received waveforms throughout a portion of the medium is performed by arithmetic, geometric, or other approximation processes (1210). In an optional process, particularly preferred in animal experimentation, contrast reagents, visible under some form of imaging such as ultrasound or Magnetic Resonance (MRI), may be inserted into the medium (1230) and monitored (1235) to observe the focal effects of the soundwave design. The design method, such as the weights used in a filter, may then be altered by a learning method such as a neural network (1238). Such a process could be used to improve the accuracy of the Shepherding process.

Figure 10:
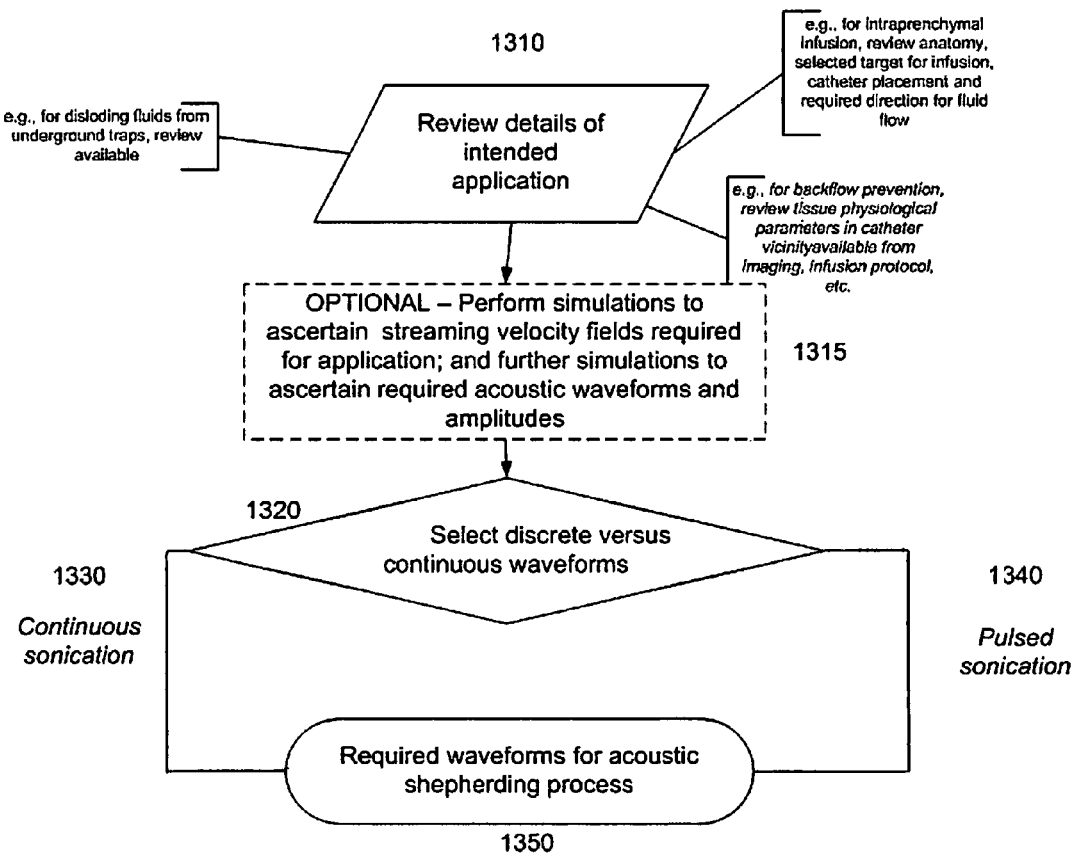
FIG. 10 shows different temporal protocols for the Acoustic Shepherding process.

In FIG. 10, it is indicated in the flow diagram that different applications may call for fundamentally different time sequences for the Acoustic Shepherding protocol. Thus have we envisaged in the practice of the present technology that a pulsed mode with periodic or intermittent pulses (termed the Nudging mode) as well as one with continuous transmission (which can be termed the Sweeping mode).

These methods may be practiced wherein the (a) at least one receiver is positioned along a catheter, and (b) where a drug or therapeutic particle is either (i) injected into a peripheral blood vessel and enters into catheterized vessels by standard pharmacokinetic phenomena or ii) introduced into parenchyma by perforating a vein by a component associated with the catheter. Also, at least one algorithm may be contained in software or hardwired circuits in a communication link with the processor is used to optimize the focused power for safe and appropriate blood brain barrier alteration, or wherein the software or hardwired circuits further includes pharmacokinetic phenomena to ensure adequate dosing and residence of the drug or therapeutic molecule in CNS tissue. At least one algorithm contained in software or hardwired circuits in a communication link with the processor may be used to optimize at least one of (i) the focused power for safe and appropriate blood brain barrier alteration, and (ii) includes pharmacokinetic phenomena to ensure adequate dosing and residence of the drug or therapeutic molecule in CNS tissue. T modified waveform pulse may be received within or adjacent to a volume of the tissue within the geometric form defined by at least two receiver locations so that a delivered portion of drugs is retained within the said volume of the tissue for a length of time longer than predictable for diffusion and perfusion factors in the volume without transmission of the modified waveform.

Although specific examples of materials, components, subcomponents, times, frequencies, temperatures and tissue locations have been provided in the detailed descriptions herein, this information represents only specific examples within the broad generic concepts disclosed herein and claimed hereafter. These specific terms are representative of generic concepts and are not to be interpreted as limitations on the scope of practice and claims of the technology. Each and every reference cited herein are incorporated herein by reference in their entirety.

The invention claimed is:

1. A method for controlling mass movement of fluid material within a field of interest comprising: (i) transmitting at least one original signal of sound waves transmitted from at least one array of transceivers located outside of a field of interest, or from at least one transceiver located inside a field of interest; (ii) receiving the at least one original signal with at least one receiver or transceiver within the field of interest as a received signal; or receiving the at least one original signal in parallel with multiple transceivers located outside the field of interest if the said original signal is transmitted from within the field of interest; (iii) a processor processing the at least one received original signal by acoustic time-reversal methods to generate a signal content relationship between the original signal and the at least one received signal; (iv) using the generated signal content relationship to design a modified acoustic waveform that will produce a specific acoustic effect in the field of interest near the at least one receiver or transceiver, respectively; and (v) transmitting the modified acoustic waveform from the at least one array of transmitters outside of the field of interest to modify mass movement of materials within the field of interest by focusing pulses of ultrasound and causing mass migration of the fluid material beyond a focus point of the modified acoustic waveform within the field of interest and without damage to tissue.

2. The method of claim 1 wherein the modified acoustic waveform is derived by optimization and approximation methods executed by a processor from transmission of waveforms, and received signals therefrom between transmitter and receiver sets, models of noise and correlations, and mathematical optimization techniques, wherein the field of interest is tissue including internal organs of living beings and the absence of damage to tissue is performed by the focused pulses not having sufficient energy to damage tissue.

3. The method of claim 2 where the tissue is brain parenchyma, the at least one repositionable transmitter array is arranged on the outside of a skull of a live patient, and the at least one receiver is at pre-determined positions along an axis of one or more catheters introduced into the brain parenchyma.

4. The method of claim 3 wherein the design of the waveform is obtained by phase modulation of excitation from an array of transmitters that creates a pressure gradient to persist to cause mass movement from a desired location within a medium within the region of interest.

5. The method of claim 4 wherein the design of the waveform is obtained by amplitude modulation of excitation of a transmitter or array of transmitters that creates a pressure gradient that persists and causes mass movement to occur from a desired location within a medium within the region of interest.

6. The method of claim 2 wherein a contrast agent visible to ultrasound or other radiological imaging is introduced and the contrast agent monitored, such monitoring being combined with a control technique selected from a group consisting of statistical estimation and neural networks to modify the transmitted waveforms to optimized the acoustic effect within the medium, and wherein the waveform to be transmitted is updated and refined after a subsequent transmission of at least one modified waveform pulse by software learning methods performed on received modified waveform pulses at the receivers.

7. The method of claim 6 where the transmitter array is one of a multiplicity of transmitter arrays positioned outside the skull, with at least 32 transmitters within the multiplicity of transmitter arrays.

8. The method of claim 6 wherein the design of the waveform is obtained by phase modulation of excitation from an array of transmitters that creates a pressure gradient to persist to cause mass movement from a desired location within a medium within the region of interest.

9. The method of claim 2 in which there is more than one receiver/transmitter along an axis of a catheter, and transmission protocol for the at least one external transmitter array introduces a time sequence of decreasing pressure amplitudes at various receiver locations, to induce a net direction of flow in a vicinity of at least one of the more than one internal receivers/transmitters.

10. The method of claim 2 in which the time reversed waveform is transmitted with an approximation of amplitudes so that the modified waveform pulse is received by the tissue at a desired point between or beyond the location of the at least two internal receiver or transceivers.

11. The method of claim 10 in which the desired point is optimized by a learning method for obtaining an approximate beam design, wherein a contrast agent visible to ultrasound or other radiological imaging is introduced and the contrast agent monitored, such monitoring being combined with a control technique such as available from statistical estimation, neural networks and other learning methods to modify the transmitted waveforms to optimize the acoustic effect within the medium.

12. The method of claim 10 wherein the modified waveform pulse is received within or adjacent to a volume of the tissue within the geometric form defined by at least two receiver locations so that a delivered portion of drugs is retained within the said volume of the tissue for a length of time longer than predictable for diffusion and perfusion factors in the volume without transmission of the modified waveform.

13. The method of claim 2 in which a multiplicity of transmitter arrays is used to enhance amplitude of the pulse at a specific internal receiver location when a time-reversed waveform is provided to at least some of several transmitters, and the signal is recorded at the specific internal receiver location.

14. The method of claim 2 wherein multiple receivers are positioned along catheters and the catheters are introduced into blood vessels, the effect of the transmitted ultrasound reversed waveform is focused, transmission of the focused transmitted waveform causing location specific alteration of blood brain barrier permeability so that drugs introduced into blood vessels is delivered into a central nervous system.

15. The method of claim 14 wherein at least one algorithm contained in software or hardwired circuits in a communication link with the processor is used to optimize the focused power for safe and appropriate blood brain barrier alteration.

16. The method of claim 14 wherein the design of the waveform is obtained by amplitude modulation of excitation of a transmitter or array of transmitters that creates a pressure gradient that persists and causes mass movement to occur from a desired location within a medium within the region of interest.

17. The method of claim 2 wherein the (a) at least one receiver is positioned along a catheter, and (b) where a drug or therapeutic particle is either (i) injected into a peripheral blood vessel and enters into catheterized vessels by standard pharmacokinetic occurrences or ii) introduced into parenchyma by perforating a vein by a component associated with the catheter.

18. The method of claim 17 where a bolus of drug encapsulated in a bubble or other liposomal capsule is injected into the peripheral blood vessel, and the ultrasonic waveform guides the capsule to desired locations in the endovascular system, the final delivery of the drug being accomplished by any of a number of schemes including sonoporation.

19. The method of claim 18, wherein the software or hardwired circuits further includes pharmacokinetic occurrences to ensure adequate dosing and residence of the drug or therapeutic molecule in central nervous system tissue.

20. The method of claim 17, wherein at least one algorithm contained in software or hardwired circuits in a communication link with the processor is used to optimize at least one of (i) the focused power for safe and appropriate blood brain barrier alteration, and (ii) includes pharmacokinetic occurrences to ensure adequate dosing and residence of the drug or therapeutic molecule in central nervous system tissue.

21. The method of claim 2 where the tissue is brain parenchyma, the transmitter array comprises at least three multiple transmitters arranged on outside of the skull, and the at least one receiver comprises encapsulated objects arranged at positions in blood vessels, the encapsulated objects being guided to the positions by magnetic stereotaxis; and then the ultrasound is focused by the time reversal for alteration of blood brain barrier permeability, causing drugs introduced into blood vessels to be delivered into central nervous system regions of the patient.

22. The method of claim 2, where the tissue is brain parenchyma, the transmitter array is arranged on the outside of the skull, and the at least one receiver is an encapsulated object arranged at positions within brain tissue, the encapsulation having migration restraining physical elements of chemically active functionality to restrain migration of the receivers.

23. The method of claim 2 wherein a design of the waveform is obtained by amplitude modulation of excitation of a transmitter or array of transmitters that creates a pressure gradient that persists and causes mass movement to occur from a desired location within a medium within the region of interest.

24. The method of claim 1 wherein the tissue comprises the prostate and pressure is directed from inside the prostate outwardly to reduce amounts of fluids entering a prostatic urethra.

25. The method of claim 1, wherein the field of interest is a land mass or human constructions containing trapped fluids.

26. The method of claim 1 in which (iii) and (iv) are selected from the group consisting of approximations, estimations, Fourier transformation, wavelet transforms, and spectral transforms or wherein the determined manner of step (iv) is selected from the group consisting of including scaling, normalization, and amplification.

27. The method of claim 1 wherein the internal transceivers are acoustically reflective sound sources in the form of microbubbles or cavitating bubbles introduced into the field of interest.

28. The method of claim 1 wherein the transmitted waveforms have a continually moving focus to aid the streaming of material or fluid across a region of interest.

29. The method of claim 1 wherein the design of the waveform is obtained by amplitude modulation of excitation of a transmitter or array of transmitters that creates a pressure gradient that persists and causes mass movement to occur from a desired location within a medium within the region of interest.

* * * * *